US012322049B2

(12) United States Patent
Katsuki et al.

(10) Patent No.: US 12,322,049 B2
(45) Date of Patent: Jun. 3, 2025

(54) MEDICAL IMAGE PROCESSING SYSTEM, SURGICAL IMAGE CONTROL DEVICE, AND SURGICAL IMAGE CONTROL METHOD

(71) Applicant: SONY GROUP CORPORATION, Tokyo (JP)

(72) Inventors: Shinji Katsuki, Tokyo (JP); Kana Matsuura, Tokyo (JP); Motoaki Kobayashi, Tokyo (JP)

(73) Assignee: SONY GROUP CORPORATION, Tokyo (JP)

( * ) Notice: Subject to any disclaimer, the term of this patent is extended or adjusted under 35 U.S.C. 154(b) by 196 days.

(21) Appl. No.: 18/000,914

(22) PCT Filed: May 21, 2021

(86) PCT No.: PCT/JP2021/019308
§ 371 (c)(1),
(2) Date: Dec. 6, 2022

(87) PCT Pub. No.: WO2021/256168
PCT Pub. Date: Dec. 23, 2021

(65) Prior Publication Data
US 2023/0222740 A1    Jul. 13, 2023

(30) Foreign Application Priority Data

Jun. 15, 2020   (JP) ................................ 2020-103123

(51) Int. Cl.
*G06T 19/00* (2011.01)
*G06T 17/00* (2006.01)
(Continued)

(52) U.S. Cl.
CPC ............ *G06T 19/006* (2013.01); *G06T 17/00* (2013.01); *G06T 19/20* (2013.01); *H04N 13/361* (2018.05);
(Continued)

(58) Field of Classification Search
CPC ....... G06T 19/006; G06T 19/20; G06T 17/00; G06T 2210/41; G06T 2219/2012; G06T 2219/2016; H04N 13/361
See application file for complete search history.

(56) References Cited

U.S. PATENT DOCUMENTS

| 2001/0031919 A1* | 10/2001 | Strommer | .............. A61B 8/463 |
|---|---|---|---|
| | | | 600/424 |
| 2008/0119728 A1* | 5/2008 | Frenkel | ................ A61B 6/5235 |
| | | | 600/426 |
| 2020/0138518 A1* | 5/2020 | Lang | ...................... A61B 90/37 |

FOREIGN PATENT DOCUMENTS

| JP | 2017-502807 A | 1/2017 |
|---|---|---|
| JP | 2017-512554 A | 5/2017 |

(Continued)

OTHER PUBLICATIONS

International Search Report and Written Opinion of PCT Application No. PCT/JP2021/019308, issued on Aug. 10, 2021, 11 pages of ISRWO.

*Primary Examiner* — Michelle Chin
(74) *Attorney, Agent, or Firm* — CHIP LAW GROUP

(57) ABSTRACT

A medical image processing system includes an acquisition unit that acquires a real-time 3D surgical image of an operation site stereoscopically viewable by a surgeon and a 3D model image that is a stereoscopic CG image associated with the 3D surgical image, and a superimposition unit that performs enhancement such that the location of the 3D model image at predetermined spatial positions is enhanced with respect to the 3D surgical image or the 3D model image at the start of superimposition of the 3D model image at the predetermined spatial positions when the 3D surgical image is stereoscopically viewed on the basis of information set for the 3D model image.

12 Claims, 15 Drawing Sheets

(51) Int. Cl.
*G06T 19/20* (2011.01)
*H04N 13/361* (2018.01)

(52) U.S. Cl.
CPC .. *G06T 2210/41* (2013.01); *G06T 2219/2012* (2013.01); *G06T 2219/2016* (2013.01)

(56) References Cited

FOREIGN PATENT DOCUMENTS

| | | |
|---|---|---|
| JP | 2018-532467 A | 11/2018 |
| JP | 2019-162339 A | 9/2019 |
| JP | 2020-022563 A | 2/2020 |
| WO | 2018/012080 A1 | 1/2018 |
| WO | 2018/195216 A1 | 10/2018 |

\* cited by examiner

MEDICAL IMAGE PROCESSING SYSTEM, SURGICAL IMAGE CONTROL DEVICE, AND SURGICAL IMAGE CONTROL METHOD

CROSS REFERENCE TO RELATED APPLICATIONS

This application is a U.S. National Phase of International Patent Application No. PCT/JP2021/019308 filed on May 21, 2021, which claims priority benefit of Japanese Patent Application No. JP 2020-103123 filed in the Japan Patent Office on Jun. 15, 2020. Each of the above-referenced applications is hereby incorporated herein by reference in its entirety.

TECHNICAL FIELD

The present disclosure relates to a medical image processing system, a surgical image control device, and a surgical image control method.

BACKGROUND ART

A surgical style for performing an operation while viewing a surgical image of an operation site captured by an endoscope or a surgical microscope is proposed. At this point, in order to allow a surgeon to more accurately recognize the position of a blood vessel or the like, the surgical image needs to be displayed as a 3D cross image or a right-eye image and a left-eye image for the surgeon such that the surgeon can three-dimensionally recognize the operation site from the image (hereinafter referred to as a 3D surgical image).

CITATION LIST

Patent Literature

[PTL 1]
JP 2020-22563 A
[PTL 2]
JP 2019-162339 A

SUMMARY

Technical Problem

However, when a 3D model image presenting navigation or the like is superimposed on a 3D surgical image, a texture mismatch between a real image and the 3D model image or inconsistencies in brightness may cause unnaturalness in the vision of a surgeon. This may lead to difficulty in recognizing, in the brain of the surgeon, the position of the 3D model image in a space indicated by the 3D surgical image. In other words, the spatial superimposition position of the 3D model image in the 3D surgical image may be different from the spatial superimposition position of the 3D model image in the brain of the surgeon or the 3D model image may fail to be three-dimensionally recognized. Thus, an aspect of the present disclosure provides a medical image processing system that facilitates the recognition of the position of a 3D model image in a 3D surgical image.

Solution to Problem

In order to solve the problem, the present disclosure provides a medical image processing system including: an acquisition unit that acquires a real-time 3D surgical image of an operation site stereoscopically viewable by a surgeon and a 3D model image that is a stereoscopic CG image associated with the 3D surgical image; and
a superimposition unit that performs enhancement such that the location of the 3D model image at predetermined spatial positions is enhanced with respect to the 3D surgical image or the 3D model image at the start of superimposition of the 3D model image at the predetermined spatial positions when the 3D surgical image is stereoscopically viewed on the basis of information set for the 3D model image.

The medical image processing system may further include a display device configured to display the 3D surgical image and the 3D model image that are superimposed by the superimposition unit.

The superimposition unit may generate the 3D model image that moves back and forth in the depth direction with respect to the predetermined spatial positions.

The superimposition unit may generate the 3D model image that gradually decreases in the amount of back-and-forth movement in the depth direction with respect to the predetermined spatial positions.

The superimposition unit may change, according to the size of the 3D model image, an amount of back-and-forth movement in the depth direction with respect to the predetermined spatial positions.

The superimposition unit may rotate the 3D model image with respect to the predetermined spatial positions.

The superimposition unit may change the color of the 3D model image with respect to the predetermined spatial positions.

The superimposition unit may gradually change the color of the 3D model image with respect to the predetermined spatial positions.

The superimposition unit may change at least one of the color and the spatial frequency of the 3D surgical image when performing the enhancement.

The medical image processing system may further include at least one of an endoscope and a surgical microscope that capture an original image used for generating the 3D surgical image.

In order to solve the problem, the present disclosure provides a surgical image control device including: an acquisition unit that acquires a real-time 3D surgical image of an operation site stereoscopically viewable by a surgeon and a 3D model image that is a stereoscopic CG image associated with the 3D surgical image; and a superimposition unit that performs enhancement such that the location of the 3D model image at predetermined spatial positions is enhanced with respect to the 3D surgical image or the 3D model image at the start of superimposition of the 3D model image at the predetermined spatial positions when the 3D surgical image is stereoscopically viewed on the basis of information set for the 3D model image.

In order to solve the problem, the present disclosure provides a surgical image control method including: acquiring a real-time 3D surgical image of an operation site stereoscopically viewable by a surgeon and a 3D model image that is a stereoscopic CG image associated with the 3D surgical image; and conducting superimposition that performs enhancement such that the location of the 3D model image at predetermined spatial positions is enhanced with respect to the 3D surgical image or the 3D model image at the start of superimposition of the 3D model image at the predetermined spatial positions when the 3D surgical image is stereoscopically viewed on the basis of information set for the 3D model image.

DESCRIPTION OF EMBODIMENTS

An embodiment of a medical image processing system, a surgical image control device, and a surgical image control method will be described below with reference to the accompanying drawings. Hereinafter, main components of the medical image processing system, the surgical image control device, and the surgical image control method will be mainly described, but the medical image processing system, the surgical image controller, and the surgical image control method may have components or functions that are not illustrated or described. The following description does not exclude components or functions that are not illustrated or described.

Figure 1:
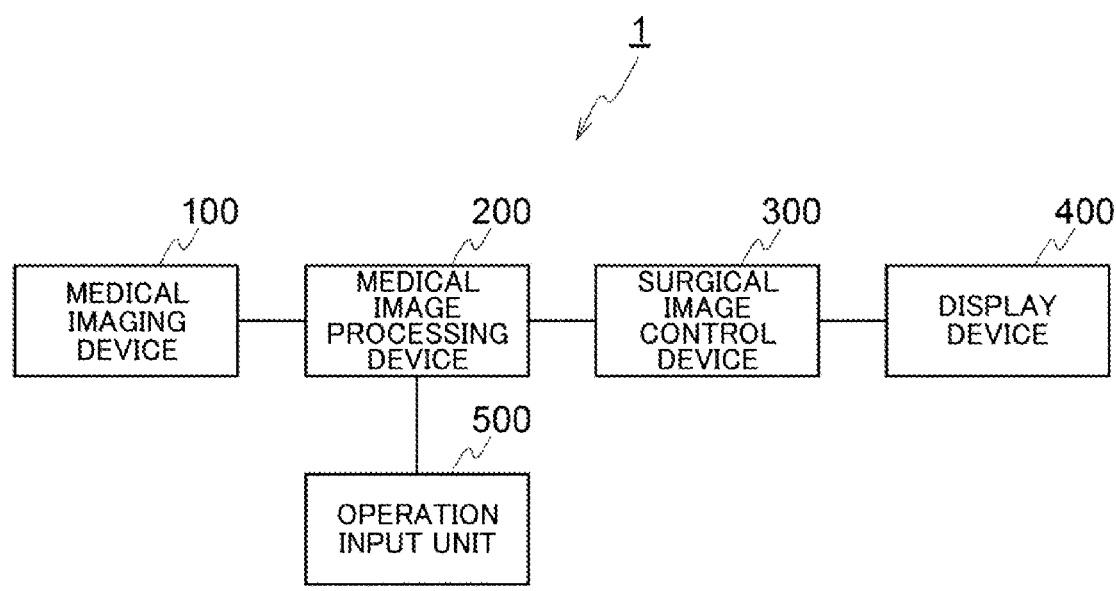
FIG. 1 is a block diagram of a medical image processing system 1 according to the present embodiment.

FIG. 1 is a block diagram of a medical image processing system 1 according to the present embodiment. As illustrated in FIG. 1, the medical image processing system 1 is a system capable of displaying, for a surgeon, a surgical image as a 3D cross image or a right-eye image and a left-eye image. The medical image processing system 1 includes a medical imaging device 100, a medical image processing device 200, a surgical image control device 300, a display device 400, and an operation input unit 500.

The medical imaging device 100 is an imaging device capable of imaging a human body. The medical imaging device 100 is, for example, an endoscope and a surgical microscope and can capture an image in real time during surgery. The detail of the medical imaging device 100 will be described later.

The medical image processing device 200 generates a real-time 3D surgical image of an operation site, which can be stereoscopically viewed by a surgeon, by using an original image captured by the medical imaging device 100. The medical image processing device 200 also generates a 3D model image presenting navigation or the like in the 3D surgical image. The 3D model image is a 3D model including, for example, a blood vessel and an organ that are to be transplanted. The detail of the medical image processing device 200 will be also described later.

The surgical image control device 300 performs control to superimpose the 3D surgical image and the 3D model image that are generated by the medical image processing device 200 and display the images on the display device 400. The detail of the surgical image control device 300 will be also described later.

The display device 400 is a device capable of providing 3D display and displays various kinds of information. For example, the display device 400 superimposes the 3D surgical image and the 3D model image, which are generated by the surgical image control device 300, and outputs a medical image and a GUI (Graphical User Interface) or the like for receiving various operations from an operator.

The operation input unit 500 receives various input operations from the operator, converts the received input operation into an electric signal, and outputs the electric signal to the medical image processing device 200. For example, the operation input unit 500 receives, from the operator, the placement position of the 3D model image, the display conditions of the 3D model image, the construction conditions of the 3D surgical image, and image processing conditions for superimposing the 3D surgical image and the 3D model image. The operation input unit 500 is implemented by, for example, a mouse, a keyboard, a trackball, a switch, a button, and a joystick.

Figure 2:
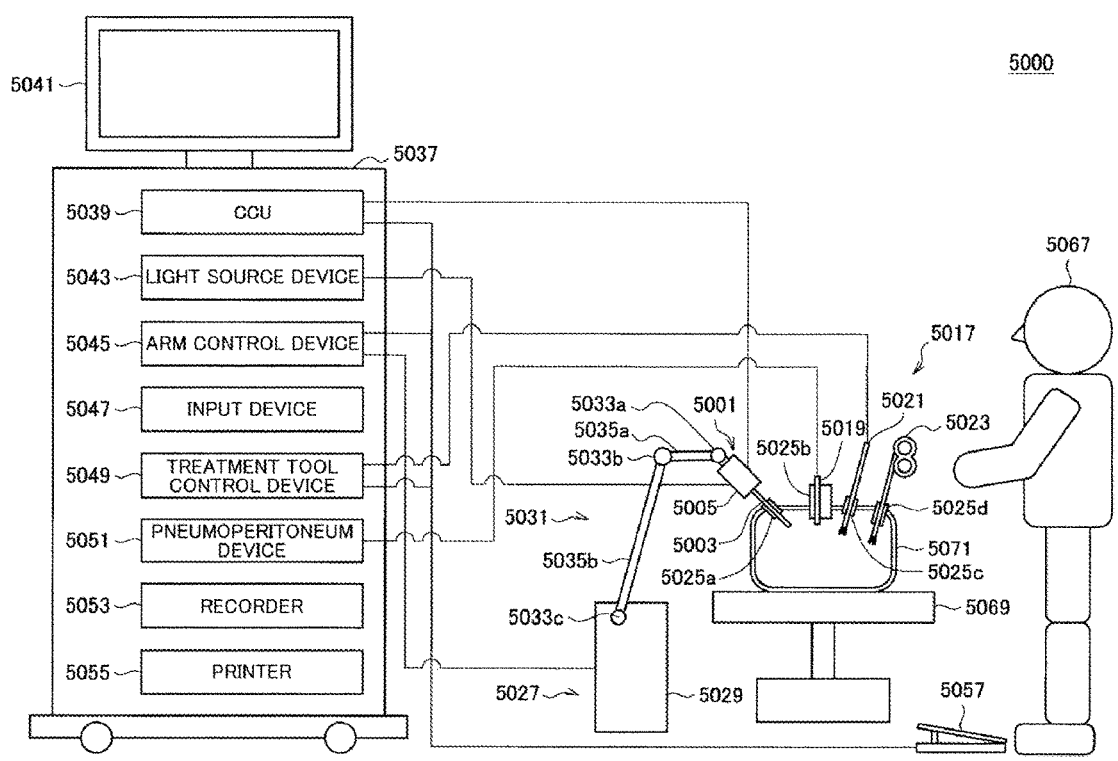
FIG. 2 illustrates an example of a schematic configuration of an endoscopic surgery system to which the technique according to the present disclosure is applicable.
Figure 3:
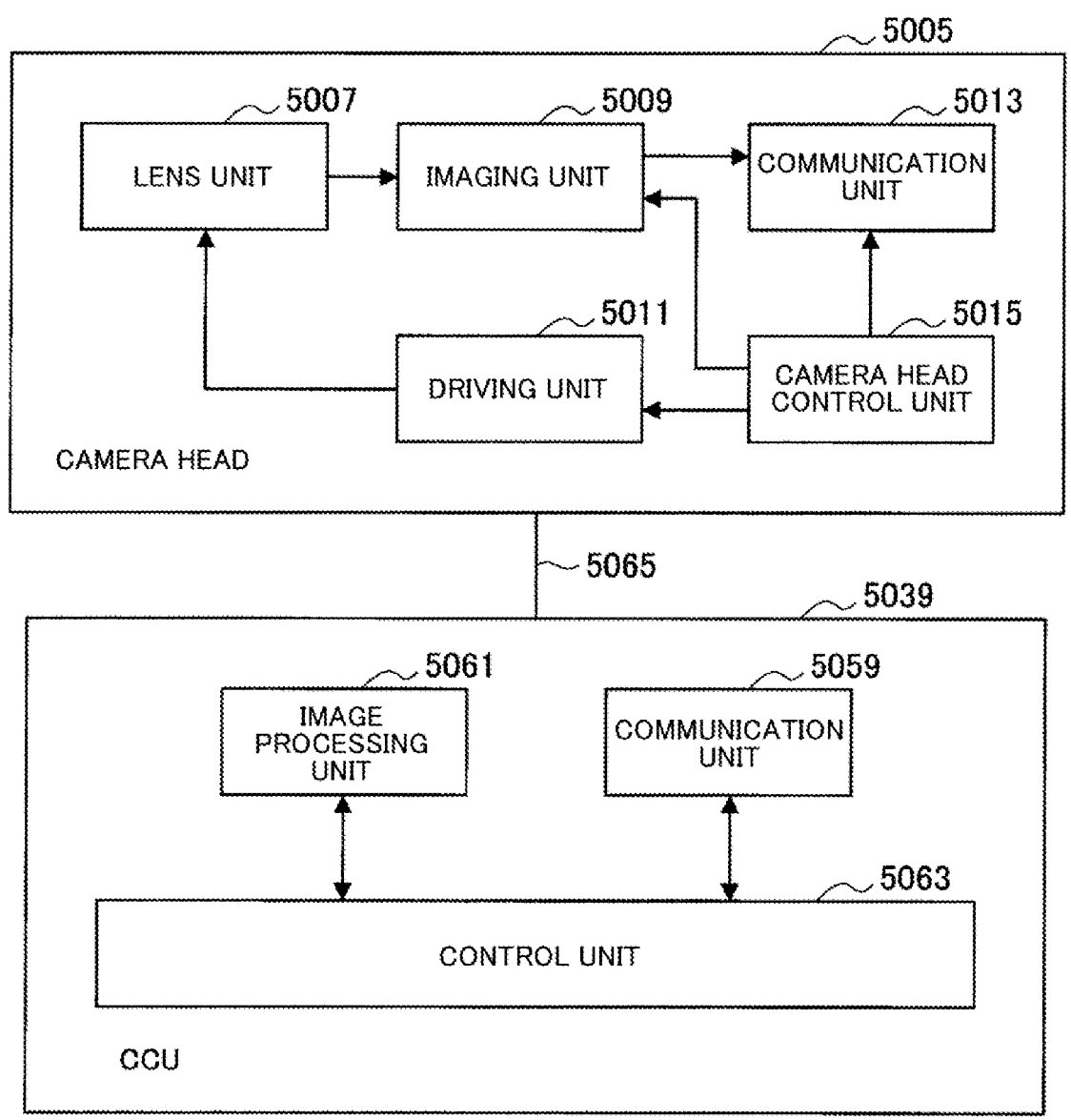
FIG. 3 is a block diagram illustrating an example of a functional configuration of a camera head and a CCU illustrated in FIG. 2.

Referring to FIGS. 2 and 3, a configuration example of an endoscopic surgery system 5000 including the medical image processing system 1 will be described below. In the endoscopic surgery system 5000 according to the present embodiment, an endoscope 5001 corresponds to the medical imaging device 100, a CCU 5039 corresponds to the medical image processing device 200 and the surgical image control device 300, and a display device 5041 corresponds to the display device 400. The typical functions of the CCU 5039 will be first described in detail, and then the characteristic functions thereof will be specifically described later with reference to FIGS. 4, 5, 6, 7, 8, 9, 10A, 10B, 11A, 11B, 11C, 12A, 12B, 13A, 13B, 13C, 14A, 14B, and 14C.

FIG. 2 illustrates a schematic configuration example of the endoscopic surgery system 5000 to which the technique of the present disclosure is applicable. FIG. 2 illustrates a surgeon (doctor) 5067 who conducts a surgical operation on a patient 5071 on a patient bed 5069 by using the endoscopic surgery system 5000. As illustrated in FIG. 2, the endoscopic surgery system 5000 includes the endoscope 5001, other surgical instruments 5017, a support arm device 5027 that supports the endoscope 5001, and a cart 5037 that accommodates various devices for an endoscopic surgical operation.

In endoscopic surgery, a plurality of tubular laparotomy devices called trocars 5025a to 5025d are punctured into the abdominal wall, instead of an abdominal operation of cutting the abdominal wall. Then, a lens-barrel 5003 of the endoscope 5001 and the other surgical instruments 5017 are inserted into the body cavity of the patient 5071 from the trocars 5025a to 5025d. In the illustrated example, a pneumoperitoneum tube 5019, an energy treatment tool 5021, and a forceps 5023 are inserted into the body cavity of the patient 5071 as the other surgical instruments 5017. In addition, the energy treatment tool 5021 is a treatment tool for performing cutting and peeling of tissue, sealing of blood vessels, or the like by using a high-frequency current or ultrasonic vibration. However, the surgical instrument 5017 illustrated in the drawing is merely an example, and various surgical instruments that are generally used in endoscopic surgical operations, such as tweezers and a retractor, may be used as the surgical instruments 5017.

An image of a surgical part within the body cavity of the patient 5071 imaged by the endoscope 5001 is displayed on the display device 5041. The surgeon 5067 performs treatment such as cutting-out of an affected part, using the energy treatment tool 5021 or the forceps 5023 while viewing the image of the surgical part displayed on the display device 5041 in real time. The pneumoperitoneum tube 5019, the energy treatment tool 5021, and the forceps 5023 are supported by the surgeon 5067 or an assistant or the like during a surgical operation, though the state of the supported instruments is not illustrated.

(Support Arm Device)

The support arm device 5027 includes an arm part 5031 extending from a base part 5029. In the illustrated example, the arm part 5031 includes joints 5033*a*, 5033*b*, and 5033*c* and links 5035*a* and 5035*b* and is driven under the control of an arm control device 5045. The endoscope 5001 is supported by the arm part 5031, and the position and posture thereof are controlled by the arm part 5031. Thus, the position of the endoscope 5001 can be stably fixed.

(Endoscope)

The endoscope 5001 includes the lens-barrel 5003 configured such that a region having a predetermined length is inserted into the body cavity of the patient 5071 from the tip end, and a camera head 5005 connected to the proximal end of the lens-barrel 5003. In the illustrated example, the endoscope 5001 is configured as a so-called hard mirror including the hard lens-barrel 5003. The endoscope 5001 may be configured as a so-called soft mirror including the soft lens-barrel 5003.

The tip end of the lens-barrel 5003 has an opening where an object lens is fit. A light source device 5043 is connected to the endoscope 5001. Light generated by the light source device 5043 is guided to the tip end of the lens-barrel by a light guide extending into the lens-barrel 5003 and is emitted through the object lens to an object to be observed in the body cavity of the patient 5071. The endoscope 5001 may be a direct-view mirror, a perspective-view mirror, or a side-view mirror.

The camera head 5005 includes an optical system and an imaging element. Reflected light (observation light) from an object to be observed is condensed on the image sensor by the optical system. The observation light is photoelectrically converted by the imaging element, and an electric signal corresponding to the observed light, that is, an image signal corresponding to an observed image is generated. The image signal is transmitted as RAW data to the camera control unit (CCU) 5039. The camera head 5005 has the function of adjusting a magnification and a focal distance by properly driving the optical system.

For example, for stereoscopic vision (3D display) or the like, the camera head 5005 may be provided with a plurality of imaging elements. In this case, a plurality of relay optical systems are provided in the lens-barrel 5003 in order to guide observation light to each of the imaging elements.

(Various Devices Mounted on Cart)

The CCU 5039 is configured with a CPU (Central Processing Unit) and a GPU (Graphics Processing Unit) or the like and controls the overall operations of the endoscope 5001 and the display device 5041. Specifically, the CCU 5039 performs, on the image signal received from the camera head 5005, various kinds of image processing for displaying an image based on the image signal, for example, development (demosaic processing). The CCU 5039 provides the display device 5041 with the image signal having been subjected to the image processing. In addition, the CCU 5039 transmits a control signal to the camera head 5005 and controls the driving thereof. The control signal may include information on imaging conditions such as a magnification and a focal distance.

Under the control of the CCU 5039, the display device 5041 displays an image based on the image signal having been subjected to the image processing by the CCU 5039. If the endoscope 5001 is an endoscope compatible with high-resolution imaging such as 4K (the number of horizontal pixels 3840×the number of vertical pixels 2160) or 8K (the number of horizontal pixels 7680×the number of vertical pixels 4320) and/or an endoscope compatible with 3D display, the display device 5041 may be, for the respective endoscopes, a display device capable of providing high-resolution display and/or a display device capable of providing 3D display. If the endoscope 5001 is compatible with high-resolution imaging such as 4K or 8K, a further immersive feeling can be obtained by using a display device having a size of 55 inches or larger as the display device 5041. In addition, a plurality of display devices 5041 having different resolutions and sizes may be provided depending on the application thereof.

The light source device 5043 includes, for example, a light source such as an LED (light emitting diode) and supplies irradiation light for imaging a surgical part to the endoscope 5001.

The arm control device 5045 includes a processor, e.g., a CPU and operates according to a predetermined program so as to control the driving of the arm part 5031 of the support arm device 5027 according to a predetermined control method.

An input device 5047 is an input interface for the endoscopic surgery system 5000. A user can input various kinds of information and instructions to the endoscopic surgery system 5000 via the input device 5047. For example, the user inputs various kinds of information on surgery, for example, body information on a patient and information on techniques via the input device 5047. For example, the user inputs, via the input device 5047, an instruction to drive the arm part 5031, an instruction to change the imaging conditions (the kind of irradiation light, a magnification, and a focal distance) of the endoscope 5001, and an instruction to drive the energy treatment tool 5021.

The type of input device 5047 is not limited. The input device 5047 may be various known input devices. As the input device 5047, for example, a mouse, a keyboard, a touch panel, a switch, a foot switch 5057 and/or a lever can be applied. If a touch panel is used as the input device 5047, the touch panel may be provided on the display surface of the display device 5041.

Alternatively, the input device 5047 is a device worn by a user, for example, a spectacle-type wearable device or an HMD (Head Mounted Display). Various inputs are made to the input device 5047 in response to a user's gesture and a user's line of sight that are detected by these devices. The input device 5047 further includes a camera capable of detecting a user's motion. Various inputs are made to the input device 5047 in response to a user's gesture and a user's line of sight that are detected from images captured by the camera. The input device 5047 further includes a microphone capable of picking up user's voices. Various inputs are audibly made to the input device 5047 via the microphone. In this way, the input device 5047 is configured to input various kinds of information in a noncontact manner, allowing a user (e.g., the surgeon 5067) particularly belonging to a clean area to operate a device belonging to an unclean area in a noncontact manner. The user can operate the device without removing a hand from a held surgical instrument, thereby improving user convenience.

A treatment tool control device 5049 controls the driving of the energy treatment tool 5021 for performing cauterization and incision of tissue, sealing of blood vessels, or the like. For the purpose of securing the field of view by the endoscope 5001 and securing a work space for a surgeon, a pneumoperitoneum device 5051 sends gas into the body cavity of the patient 5071 through the pneumoperitoneum tube 5019 in order to inflate the body cavity. A recorder 5053 is a device capable of recording various kinds of information on surgery. A printer 5055 is a device capable of printing various kinds of information on surgery in various formats including a text, an image, and a graph.

Hereinafter, particularly characteristic configurations in the endoscopic surgery system 5000 will be described in greater detail.

(Support Arm Device)

The support arm device 5027 includes the base part 5029 serving as a base, and the arm part 5031 extending from the base part 5029. In the illustrated example, the arm part 5031 includes the plurality of joints 5033a, 5033b, and 5033c and the plurality of links 5035a and 5035b connected to each other by the joint 5033b. In FIG. 2, the configuration of the arm part 5031 is simplified for ease of explanation. Actually, the shapes, number, and arrangement of the joints 5033a to 5033c and the links 5035a and 5035b and the directions of the rotation axes of the joints 5033a to 5033c can be properly set such that the arm part 5031 has a desired degree of freedom. For example, the arm part 5031 can be preferably configured to have at least 6 degrees of freedom. This can freely move the endoscope 5001 within a movable range of the arm part 5031, thereby inserting the lens-barrel 5003 of the endoscope 5001 into the body cavity of the patient 5071 in a desired direction.

The joints 5033a to 5033c are each provided with an actuator, and the joints 5033a to 5033c are each configured to rotate about a predetermined rotation axis by the driving of the actuator. The driving of the actuator is controlled by the arm control device 5045, thereby controlling the rotation angle of each of the joints 5033a to 5033c and controlling the driving of the arm part 5031. Thus, the position and posture of the endoscope 5001 can be controlled. At this time, the arm control device 5045 can control the driving of the arm part 5031 according to various known control methods such as force control or position control.

For example, the surgeon 5067 may properly input an operation via the input device 5047 (including the foot switch 5057) to properly control the driving of the arm part 5031 using the arm control device 5045 in response to the operation input, thereby controlling the position and the posture of the endoscope 5001. According to this control, the endoscope 5001 at the tip end of the arm part 5031 can be moved from any position to another position and then can be securely supported at the position after the movement. The arm part 5031 may be operated by a so-called master slave method. In this case, the arm part 5031 can be remotely operated by a user through the input device 5047 installed at a location remote from an operating room.

If force control is applied, the arm control device 5045 may perform so-called power assist control for receiving an external force from a user and driving the actuators of the joints 5033a to 5033c so as to smoothly move the arm part 5031 in response to the external force. Thus, when the user moves the arm part 5031 while directly touching the arm part 5031, the user can move the arm part 5031 with a relatively small force. This can more intuitively move the endoscope 5001 with a simpler operation, thereby improving user convenience.

Typically, in an endoscopic surgical operation, the endoscope 5001 is supported by a doctor called a scopist. In contrast, the position of the endoscope 5001 can be more securely fixed using the support arm device 5027 without the need for manual operations, thereby stably obtaining an image of a surgical part and smoothly performing a surgical operation.

The arm control device 5045 is not necessarily provided in the cart 5037. Moreover, the arm control device 5045 is not always a single device. For example, the arm control device 5045 may be provided for each of the joints 5033a to 5033c of the arm part 5031 of the support arm device 5027, and the driving control of the arm part 5031 may be implemented by the cooperation of the plurality of arm control devices 5045.

(Light Source Device)

The light source device 5043 supplies, to the endoscope 5001, irradiation light for imaging a surgical part. The light source device 5043 includes, for example, an LED, a laser light source, or a white light source as a combination of an LED and a laser light source. At this time, if the white light source includes a combination of RGB laser light sources, the intensity and timing of output of each color (each wavelength) can be controlled with high accuracy, thereby adjusting the white balance of a captured image in the light source device 5043. Furthermore, in this case, an object to be observed is irradiated with a laser beam emitted from each of the RGB laser light sources in a time-division manner, and the driving of the imaging element of the camera head 5005 is controlled in synchronization with the timing of irradiation, thereby capturing images corresponding to RGB in a time-division manner. The method can obtain a color image without providing a color filter in the imaging element.

In addition, the driving of the light source device 5043 may be controlled so as to change the intensity of output light at predetermined time intervals. The driving of the imaging element of the camera head 5005 is controlled in synchronization with the timing of a change of the light intensity to capture images in a time-division manner, and then the images are synthesized, thereby generating an image having a high dynamic range without so-called black crushing and overexposure.

The light source device 5043 may be configured to supply light of a predetermined wavelength band corresponding to a special light observation. In the special light observation, so-called narrow band imaging is performed, in which a predetermined tissue such as a blood vessel in a superficial portion of mucous membrane is imaged with a high contrast through irradiation of light with a narrower band than irradiation light (that is, white light) during a normal observation by using, for example, the wavelength dependence of light absorption in a body tissue. Alternatively, in the special light observation, a fluorescence observation may be made, in which an image is captured by fluorescence generated by irradiation of excitation light. In the fluorescence observation, fluorescence from a body tissue can be observed by irradiating the body tissue with excitation light (self-fluorescence observation) or a fluorescent image can be captured by locally injecting a reagent, e.g., indocyanine green (ICG) into a body tissue and irradiating the body tissue with excitation light corresponding to the fluorescence wavelength of the reagent. The light source device 5043 can be configured to supply narrow band light and/or excitation light corresponding to such a special light observation.

(Camera Head and CCU)

Referring to FIG. 3, the functions of the camera head 5005 of the endoscope 5001 and the CCU 5039 will be described in more detail. FIG. 3 is a block diagram illustrating an example of the functional configurations of the camera head 5005 and the CCU 5039 in FIG. 2.

Referring to FIG. 3, the camera head 5005 includes a lens unit 5007, an imaging unit 5009, a driving unit 5011, a communication unit 5013, and a camera head control unit 5015 as the functions thereof. The CCU 5039 includes a communication unit 5059, an image processing unit 5061, and a control unit 5063 as the functions thereof. The camera head 5005 and the CCU 5039 are connected to each other via a transmission cable 5065 so as to bidirectionally communicate with each other.

The functional configuration of the camera head 5005 will be first described below. The lens unit 5007 is an optical system provided in a portion connected to the lens-barrel 5003. Observation light from the tip end of the lens-barrel 5003 is guided to the camera head 5005 and is incident on the lens unit 5007. The lens unit 5007 is configured with a combination of a plurality of lenses including a zoom lens and a focus lens. The optical characteristics of the lens unit 5007 are adjusted so as to condense observation light on the light receiving surface of an imaging element of the imaging unit 5009. Moreover, the zoom lens and the focus lens are configured so as to move on the optical axes in order to adjust the magnification and focus of a captured image.

The imaging unit 5009 includes an imaging element and is disposed in a stage subsequent to the lens unit 5007. Observation light having passed through the lens unit 5007 is condensed on the light receiving surface of the imaging element, and an image signal corresponding to an observation image is generated by photoelectric conversion. The image signal generated by the imaging unit 5009 is provided to the communication unit 5013.

The imaging element constituting the imaging unit 5009 is, for example, a CMOS (Complementary Metal Oxide Semiconductor) image sensor that has a Bayer array and can perform color imaging. The imaging element may be, for example, an imaging element compatible with high-resolution imaging of 4K or more. An image of a surgical part is obtained with high resolution, and thus the surgeon 5067 can recognize the state of the surgical part in more detail and facilitate a surgical operation.

Moreover, the imaging element constituting the imaging unit 5009 is configured to include a pair of imaging elements for acquiring a right-eye image signal and a left-eye image signal that correspond to 3D display. The provision of 3D display allows the surgeon 5067 to more accurately recognize the depth of biological tissue in the surgical part. If the imaging unit 5009 has a multi-plate configuration, a plurality of systems are provided for the lens unit 5007 according to the imaging elements.

The imaging unit 5009 is not necessarily provided in the camera head 5005. For example, the imaging unit 5009 may be provided right after the object lens inside the lens-barrel 5003.

The driving unit 5011 including an actuator moves the zoom lens and the focus lens of the lens unit 5007 along the optical axis by a predetermined distance under the control of the camera head control unit 5015. This can properly adjust the magnification and focus of an image captured by the imaging unit 5009.

The communication unit 5013 includes a communication device for transmitting and receiving various kinds of information to and from the CCU 5039. The communication unit 5013 transmits, as RAW data, an image signal obtained from the imaging unit 5009 to the CCU 5039 through the transmission cable 5065. At this point, the image signal is preferably transmitted by optical communications to display a captured image of a surgical part with low latency. This is because the surgeon 5067 performs a surgical operation while observing the state of an affected part through the captured image during the surgical operation and thus a moving image of a surgical part needs to be displayed as fast as possible to perform a safer and more reliable surgical operation. In the case of optical communications, the communication unit 5013 is provided with a photoelectric conversion module that converts an electric signal into an optical signal. An image signal is converted into an optical signal by the photoelectric conversion module and then is transmitted to the CCU 5039 through the transmission cable 5065.

Moreover, the communication unit 5013 receives a control signal for controlling the driving of the camera head 5005 from the CCU 5039. The control signal includes information on imaging conditions such as information indicating designation of a frame rate of a captured image, information indicating designation of an exposure value during imaging, and/or information indicating designation of a magnification and focus of a captured image. The communication unit 5013 provides the received control signal to the camera head control unit 5015. The control signal received from the CCU 5039 may also be transmitted by optical communications. In this case, the communication unit 5013 is provided with a photoelectric conversion module that converts an optical signal into an electric signal, and the control signal is converted into an electric signal by the photoelectric conversion module and is then provided to the camera head control unit 5015.

The imaging conditions such as a frame rate, an exposure value, a magnification, and a focus are automatically set by the control unit 5063 of the CCU 5039 on the basis of the acquired image signal. In other words, the endoscope 5001 is equipped with so-called AE (Auto Exposure), AF (Auto Focus), and AWB (Auto White Balance) functions.

The camera head control unit 5015 controls the driving of the camera head 5005 on the basis of the control signal received from the CCU 5039 through the communication unit 5013. For example, the camera head control unit 5015 controls the driving of the imaging element of the imaging unit 5009 on the basis of information indicating designation of a frame rate of a captured image and/or information indicating designation of exposure during imaging. Moreover, for example, the camera head control unit 5015 properly moves the zoom lens and the focus lens of the lens unit 5007 through the driving unit 5011 on the basis of information indicating designation of a magnification and focus of a captured image. The camera head control unit 5015 may further have the function of storing information for identifying the lens-barrel 5003 and the camera head 5005.

Configurations such as the lens unit 5007 and the imaging unit 5009 are disposed in a sealed structure with high airtightness and waterproofness, and thus the camera head 5005 can be made resistant to autoclave sterilization.

The functional configuration of the CCU 5039 will be described below. The communication unit 5059 includes a communication device for transmitting and receiving various kinds of information to and from the camera head 5005. The communication unit 5059 receives the image signal transmitted via the transmission cable 5065 from the camera head 5005. At this point, as described above, the image signal can be properly transmitted through optical communications. In this case, for optical communications, the communication unit 5059 is provided with a photoelectric conversion module that converts an optical signal into an electric signal. The communication unit 5059 provides the image signal converted into an electric signal, to the image processing unit 5061.

Moreover, the communication unit 5059 transmits a control signal for controlling the driving of the camera head 5005, to the camera head 5005. The control signal may also be transmitted by optical communications.

The image processing unit 5061 performs a variety of image processing on the image signal that is RAW data transmitted from the camera head 5005. The image processing includes, for example, a variety of known signal processing such as development, high image quality processing (e.g., band enhancement, super-resolution processing, NR (Noise Reduction) processing, and/or camera shake correction), and/or enlargement (electronic zooming). The image processing unit 5061 also performs detection on an image signal for performing AE, AF, and AWB.

The image processing unit 5061 includes a processor, e.g., a CPU or a GPU. The above-described image processing and detection can be performed by the processor operating in accordance with a predetermined program. If the image processing unit 5061 includes a plurality of GPUs, the image processing unit 5061 properly divides information on an image signal and performs image processing in parallel by means of the GPUs.

The control unit 5063 performs various kinds of control on imaging of a surgical part by the endoscope 5001 and display of a captured image of the surgical part. For example, the control unit 5063 generates a control signal for controlling the driving of the camera head 5005. At this point, if imaging conditions are inputted by a user, the control unit 5063 generates the control signal on the basis of the user input. Alternatively, if the endoscope 5001 is equipped with the AE function, the AF function, and the AWB function, the control unit 5063 properly calculates an optimum exposure value, focal distance, and white balance according to the results of detection by the image processing unit 5061 and generates the control signal.

Moreover, the control unit 5063 displays an image of a surgical part on the display device 5041 on the basis of the image signal having been subjected to the image processing by the image processing unit 5061. At this point, the control unit 5063 recognizes various objects in the surgical part image by using various image recognition techniques. For example, the control unit 5063 can recognize surgical instruments such as forceps, specific biological parts, bleeding, and mist at the time of use of the energy treatment tool 5021 by detecting the shape, color, and the like of an edge of an object included in the surgical part image. When an image of a surgical part is displayed on the display device 5041, the control unit 5063 displays various kinds of surgery support information superimposed on the image of the surgical part by using the recognition results. The superimposed surgery support information is displayed and is presented to the surgeon 5067, so that a surgical operation can be performed with greater safety and reliability.

The transmission cable 5065 connecting the camera head 5005 and the CCU 5039 is an electric signal cable that supports electric signal communications, an optical fiber that supports optical communications, or a composite cable thereof.

In the illustrated example, wire communications are performed using the transmission cable 5065. Radio communications may be performed between the camera head 5005 and the CCU 5039. In the case of radio communications, the transmission cable 5065 does not need to be routed in an operating room, and thus the transmission cable 5065 does not interfere with a movement of medical staff in the operating room.

An example of the endoscopic surgery system 5000 to which the technique according to the present disclosure is applicable has been described above. The endoscopic surgery system 5000 has been described as an example. A system to which the technique according to the present disclosure is applicable is not limited thereto. For example, the technique according to the present disclosure may be applied to a flexible endoscopy system for examination and a microsurgery system.

Figure 4:
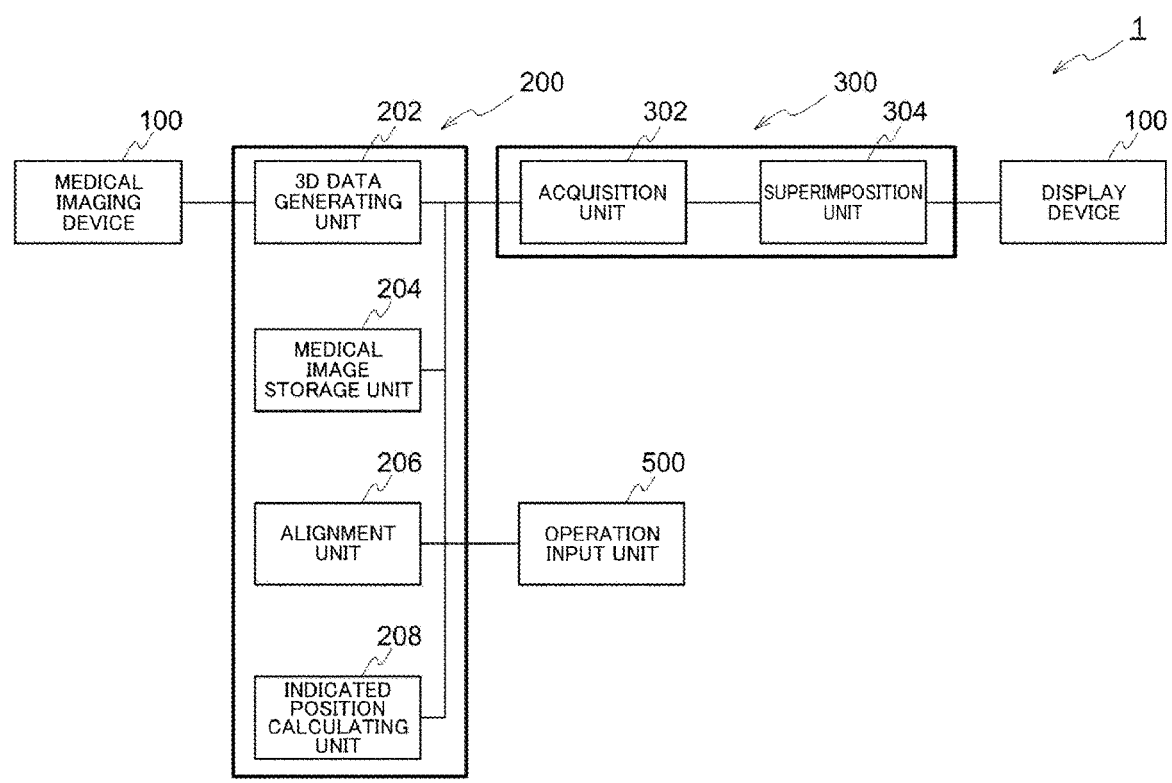
FIG. 4 is a block diagram illustrating a configuration example of a medical image processing device and a surgical image control device 0.

Referring to FIG. 4, the detail of the medical image processing device 200 and the surgical image control device 300 will be described below. FIG. 4 is a block diagram illustrating a configuration example of the medical image processing device 200 and the surgical image control device 300. As illustrated in FIG. 4, the medical image processing device 200 includes a 3D data generating unit 202, a medical image storage unit 204, and an alignment unit 206. The surgical image control device 300 includes an acquisition unit 302 and a superimposition unit 304.

The 3D data generating unit 202 generates a real-time 3D surgical image of an operation site, which can be stereoscopically viewed by a surgeon, on the basis of original image data supplied from the medical imaging device 100.

Figure 5:
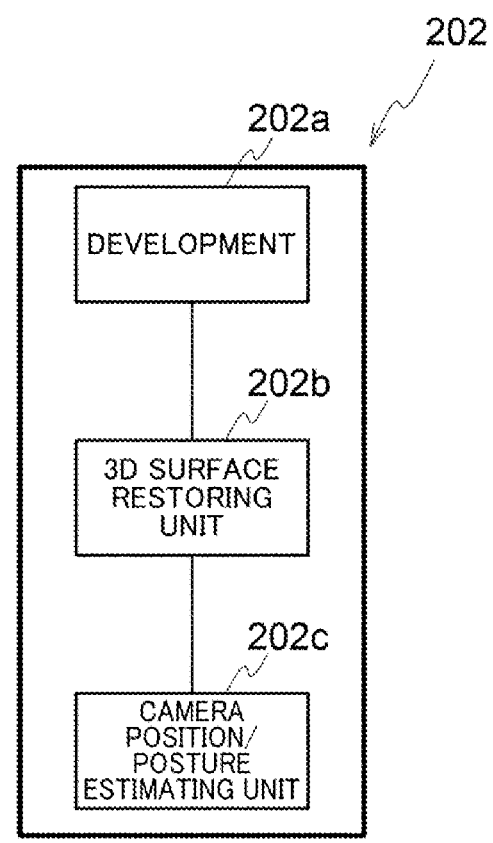
FIG. 5 is a block diagram illustrating a configuration example of a 3D data generating unit.

FIG. 5 is a block diagram illustrating a configuration example of the 3D data generating unit 202. As illustrated in FIG. 5, the 3D data generating unit 202 includes a developing unit 202a, a 3D surface restoring unit 202b, a camera position/posture estimating unit 202c.

The developing unit 202a generating image data by developing the image signals from the imaging elements in the endoscope 5001. Furthermore, the developing unit 202a generates depth data in an imaging range by parallax-based triangulation using the image signals from the imaging elements and supplies the depth data to the 3D surface restoring unit 202b and the camera position/posture estimating unit 202c.

The 3D surface restoring unit 202b acquires three-dimensional information on a subject from the depth data from the developing unit 202a. Thus, the 3D surface restoring unit 202b generates three-dimensional surface map data as a 3D surgical image. Moreover, the 3D surface restoring unit 202b updates the three-dimensional surface map data by generating three-dimensional surface map data and performing alignment in a three-dimensional space, and stores the data as three-dimensional information in the medical image storage unit 204.

The camera position/posture estimating unit 202c estimates the position and posture of the camera (estimates a movement of the endoscope 5001) by comparing the depth data obtained from the developing unit 202*a* and the three-dimensional surface map data that is generated and restored by the 3D surface restoring unit 202*b* (see PTL 2).

The medical image storage unit 204 is implemented by, for example, semiconductor memory devices such as RAM (Random Access Memory) and flash memory, a hard disk, or an optical disk. In the medical image storage unit 204, for example, 3D model images of blood vessels and organs are stored.

Specifically, stored in the medical image storage unit 204 are case data on organs used for transplantation in the past and blood vessels, and 3D model images of, for example, blood vessels and organs based on case data on artificial vessels. A 3D model image is a stereoscopic CG image. For a 3D model image, color information is set for each three-dimensional coordinate. Moreover, for a 3D model image, organ information including, for example, the outside dimensions of organs and the outside and inside diameters of blood vessels is set.

The alignment unit 206 selects a 3D model image used for display from among 3D model images stored in the medical image storage unit 204 and indicates a placement position.

Figure 6:
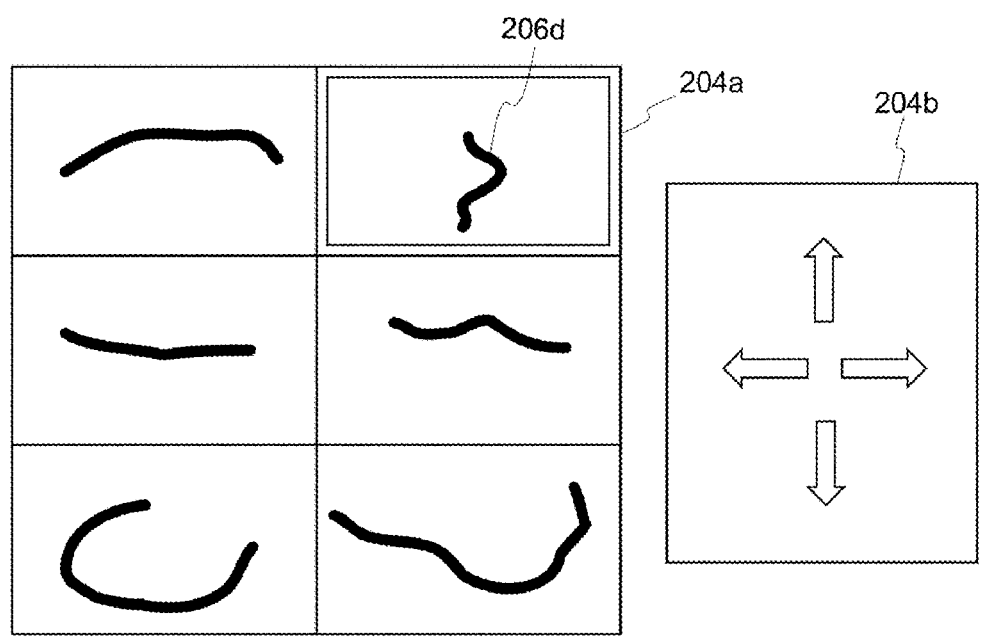
FIG. 6 illustrates an example in which a part of a 3D model image of a blood vessel is displayed on a display device, the 3D model image being stored in a specified medical image storage unit.

FIG. 6 illustrates an example in which the alignment unit 206 displays a part of a 3D model image of a blood vessel on the display device 400, the 3D model image being stored in the medical image storage unit 204. An image 204*a* is an image example of a 3D model image of a blood vessel, the 3D model image being partially displayed on the display device 400 by the alignment unit 206. An image 204*b* is an image example of a selection part operable via the operation input unit 500, the selection part being displayed on the display device 400 by the alignment unit 206. When an arrow in the image 204*b* is indicated via the operation input unit 500, the alignment unit 206 scrolls a 3D model image in the image 204*a* in the direction of the arrow.

For example, as illustrated in FIG. 6, an operator, e.g., a surgeon or an assistant operates the selection part via the operation input unit 500, the selection part being displayed as the image 204*b* on the display device 400. Thus, the operator can sequentially display and view 3D model images of blood vessels and organs or the like on the display device 400, the 3D model images being stored in the medical image storage unit 204. The operator then indicates a 3D model image used for display, via the operation input unit 500 from three-dimensional image data displayed on the display device 400. The alignment unit 206 selects a 3D model image on the basis of position information indicated via the operation input unit 500. FIG. 6 illustrates a 3D model image 206*d* in which a double-framed vessel model is selected.

The alignment unit 206 also performs processing for indicating an alignment position of a 3D model image and a 3D surgical image.

Figure 7:
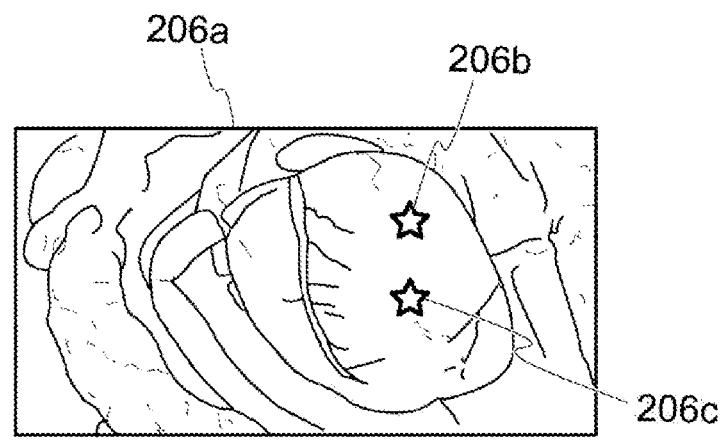
FIG. 7 illustrates an example of coordinates c indicated by an alignment unit 206.

FIG. 7 illustrates an example of coordinates 206*b* and 206*c* indicated by the alignment unit 206. As illustrated in FIG. 7, the operator indicates the indicated coordinates 206*b* and 206*c* in a 3D surgical image 206*a* via the operation input unit 500. For example, the alignment unit 206 stores the indicated coordinates 206*b* and 206*c* in the medical image storage unit 204 such that the indicated coordinates 206*b* and 206*c* are associated with the 3D model image 206*d*.

When acquiring information on the indicated coordinates 206*b* and 206*c* as operation information on a user operation, an indicated position calculating unit 208 sequentially calculates the indicated coordinates 206*b* and 206*c* on the basis of position/posture information from the 3D data generating unit 202 and the three-dimensional surface map data stored in the medical image storage unit 204. More specifically, the indicated position calculating unit 208 determines, on the three-dimensional surface map data, positions corresponding to the indicated positions of the indicated coordinates 206*b* and 206*c* on the basis of the current position and posture of the endoscope 5001 in the position/posture information. The indicated coordinates 206*b* and 206*c* that are recalculated thus are supplied in real time to the superimposition unit 304 through the acquisition unit 302.

Referring to FIG. 4 again, the acquisition unit 302 acquires a real-time 3D surgical image generated by the 3D data generating unit 202 and the indicated 3D model image 206*d* (see FIG. 6). In other words, the acquisition unit 302 acquires a real-time 3D surgical image of an operation site, which can be stereoscopically viewed by a surgeon, and the 3D model image 206*d* that is a stereoscopic CG image associated with the 3D surgical image.

At the start of superimposition of a 3D model image at predetermined spatial positions (indicated coordinates 206*b* and 206*c*) when a 3D surgical image is stereoscopically viewed on the basis of information set for the 3D model image, the superimposition unit 304 performs enhancement such that the location of the 3D model image at the predetermined spatial positions is enhanced with respect to the 3D surgical image or the 3D model image.

Figure 8:
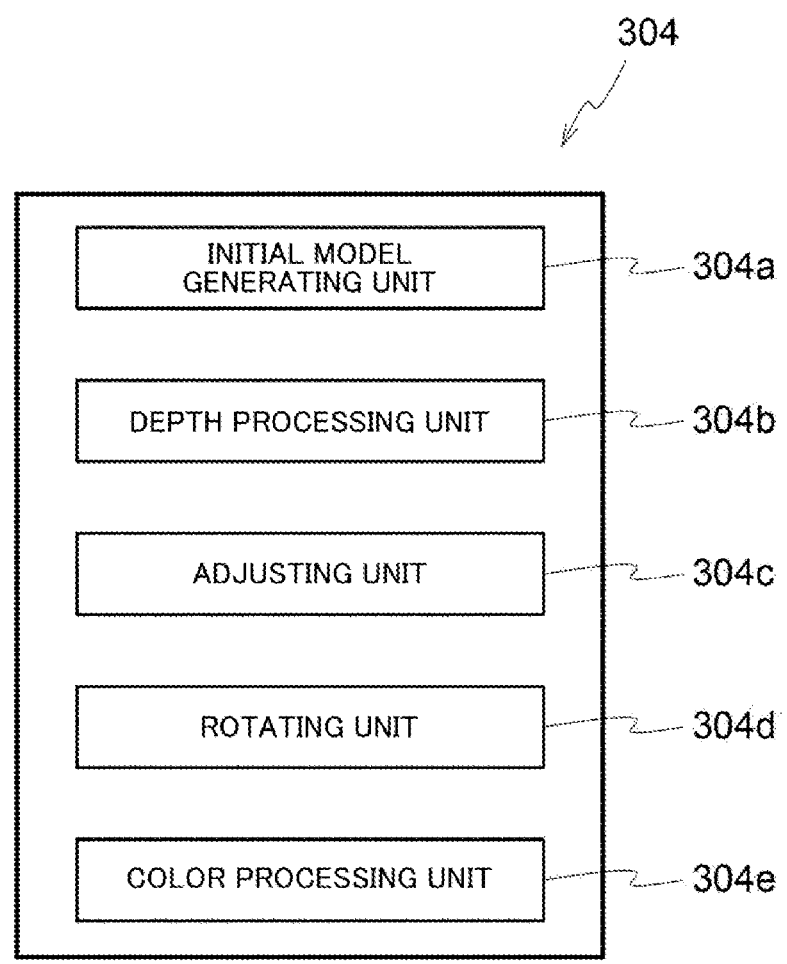
FIG. 8 is a block diagram illustrating a configuration example of a superimposition unit.

FIG. 8 is a block diagram illustrating a configuration example of the superimposition unit 304. As illustrated in FIG. 8, the superimposition unit 304 generates the 3D model image 206*d* that provides stereoscopic view of a 3D model. The superimposition unit 304 includes an initial model generating unit 304*a*, a depth processing unit 304*b*, an adjusting unit 304*c*, a rotating unit 304*d*, and a color processing unit 304*e*. For example, the superimposition unit 304 generates the 3D model image 206*d* by computer graphics (Hereinafter computer graphics may be referred to as CG).

Stereoscopic vision in the present embodiment means, for example, vergence, accommodation, binocular disparity, and motion parallax but is not thereto. Vergence is, for example, stereoscopic vision that allows perception of a depth according to the principle of triangulation from the rotation angles of right and left eyes when a point is closely observed. Accommodation is stereoscopic vision that allows perception of a depth by adjusting the focus of eyes. Binocular disparity is stereoscopic vision that allows perception of a depth according to a horizontal displacement between corresponding points in the retinal presentation of right and left eyes. Motion parallax is stereoscopic vision that allows perception of a depth on the basis of a change of a retinal image when a viewpoint moves. To achieve such stereoscopic vision, for example, a lenticular-lens monitor or a barrier monitor can be used as the display device 400. Alternatively, in the display of the 3D model image 206*d*, a method of displaying images with a horizontal parallax in the display part of the display device 400 may be used such that the images are viewed by right and left eyes, respectively, through glasses on an operator. In this case, for example, a method using polarized glasses, an anaglyph, or a liquid-crystal shutter is available.

The initial model generating unit 304*a* generates the 3D model image 206*d* on the basis of information on the 3D model image 206*d* acquired through the acquisition unit 302 and the indicated coordinates 206*b* and 206*c*. Moreover, the initial model generating unit 304*a* adjusts the size of the 3D model image 206*d* on the basis of the indicated coordinates 206*b* and 206*c*. For example, the length of a blood vessel is adjusted while keeping the outside diameter of the blood vessel on the basis of information on a vessel diameter set for the 3D model image 206d.

Figure 9:
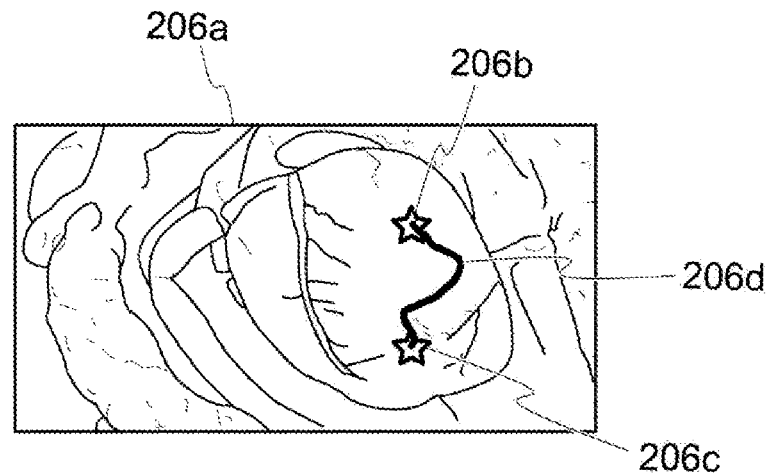
FIG. 9 illustrates the 3D model image disposed at the indicated coordinates in a 3D surgical image.

In FIG. 9, the 3D model image 206d generated by the initial model generating unit 304a is disposed at the indicated coordinates 206b and 206c in the 3D surgical image 206a. In other words, FIG. 9 illustrates a screen indicating an initial state of the 3D model image 206d disposed in the 3D surgical image 206a. Since the indicated position calculating unit 208 always calculates the indicated coordinates 206b and 206c, the initial state screen of the 3D model image 206d is disposed at the positions of the indicated coordinates 206b and 206c in the 3D surgical image 206a even if the indicated coordinates 206b and 206c are relocated.

The depth processing unit 304b displays a CG image, which moves back and forth in the 3D depth direction, on the display device 400 as the 3D model image 206d generated by the initial model generating unit 304a, and then the depth processing unit 304b disposes the CG image at the correct indicated coordinates 206b and 206c. More specifically, the depth processing unit 304b generates the 3D model image 206d that moves back and forth in the depth direction with respect to the predetermined spatial positions (indicated coordinates 206b and 206c) in the 3D surgical image 206a, and then the depth processing unit 304b superimposes the 3D model image 206d on the real-time 3D surgical image 206a.

Figure 10A:
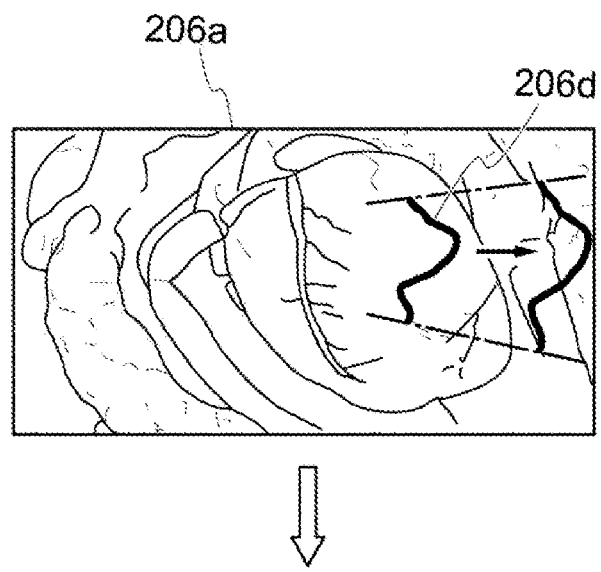
FIGS. 10A and 10B schematically illustrate an example in which a CG image generated by a depth processing unit is superimposed on the 3D surgical image.
Figure 10B:
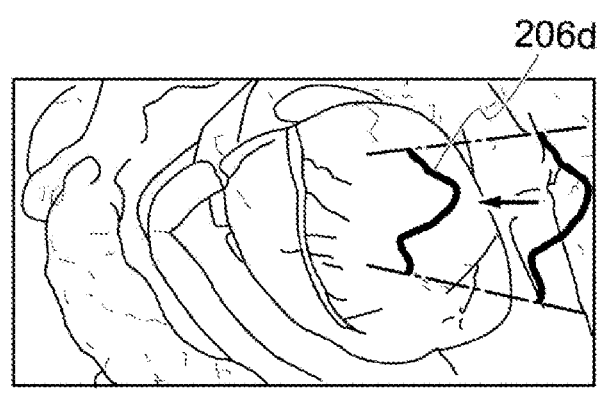

FIGS. 10A and 10B schematically illustrate an example in which a CG image generated by the depth processing unit 304b is superimposed on the 3D surgical image 206a. FIG. 10A illustrates an example in which the 3D model image 206d is moved toward an operator in the depth direction. FIG. 10B illustrates an example in which the 3D model image 206d is moved in a direction that separates from the operator in the depth direction. The display of such a CG image allows the operator to easily recognize the 3D model image 206d as a 3D image. Once the 3D model image 206d is recognized as a 3D image, the image is recognized as a 3D image even after being located at the indicated coordinates 206b and 206c. In this way, the 3D model image 206d is securely recognized as a 3D image by observers including an assistant, so that the 3D surgical image 206a and the 3D model image 206d are integrally recognized as a 3D image. This facilitates 3D observation of the 3D model image 206d. Also in this case, the indicated position calculating unit 208 always calculates the indicated coordinates 206b and 206c (see FIG. 9), so that the final state screen of the 3D model image 206d is disposed at the positions of the indicated coordinates 206b and 206c in the 3D surgical image 206a even when the indicated coordinates 206b and 206c are relocated.

Furthermore, the depth processing unit 304b changes, according to the size of the 3D model image 206d, an amount of back-and-forth movement in the depth direction with respect to the predetermined spatial positions. For example, the depth processing unit 304b increases the amount of movement with the size of the 3D model image 206d. This allows observers including an assistance to more naturally recognize the 3D model image 206d as a 3D image and secure the recognition.

The depth processing unit 304b may change an amount of back-and-forth movement in the depth direction with respect to the predetermined spatial positions (indicated coordinates 206b and 206c), according to the size of the 3D model image 206d relative to the 3D surgical image 206a. For example, the depth processing unit 304b increases the amount of movement as the size of the 3D model image 206d increases relative to the 3D surgical image 206a. This allows observers including an assistance to more naturally secure the recognition of the 3D model image 206d as a 3D image regardless of the size of the 3D model image 206d.

The adjusting unit 304c generates the 3D model image 206d that gradually decreases in the amount of back-and-forth movement in the depth direction with respect to the predetermined spatial positions (indicated coordinates 206b and 206c) in the 3D surgical image 206a, and then the adjusting unit 304c superimposes the 3D model image 206d on the real-time 3D surgical image 206a. The adjusting unit 304c may generate the 3D model image 206d that gradually decreases in the amount of back-and-forth movement in addition to the processing function of the depth processing unit 304b. In this case, the adjusting unit 304c first generates the 3D model image 206d that largely moves back and forth in the depth direction and then generates the 3D model image 206d that gradually decreases in the amount of back-and-forth movement in the depth direction with respect to the spatial positions (indicated coordinates 206b and 206c).

Figure 11A:
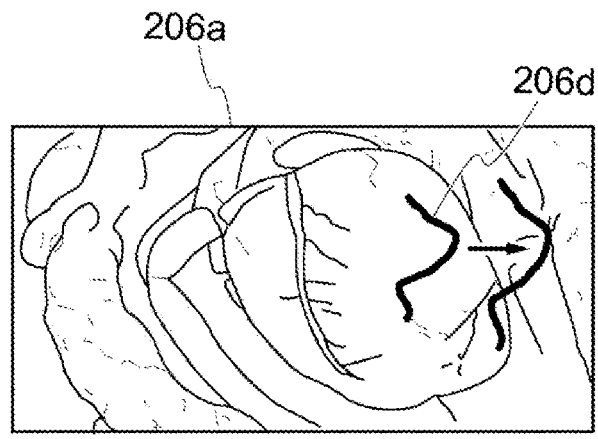
FIGS. 11A, 11B, and 11C schematically illustrate a CG image generated by an adjusting unit.
Figure 11B:
Figure 11C:

FIGS. 11A, 11B, and 11C schematically illustrate a CG image generated by the adjusting unit 304c. FIG. 11A illustrates an example in which the 3D model image 206d is moved from the spatial positions (indicated coordinates 206b and 206c) toward the operator in the depth direction. FIG. 11B illustrates an example in which the 3D model image 206d is moved from the spatial positions (indicated coordinates 206b and 206c) in a direction that separates from the operator in the depth direction. FIG. 11C illustrates an example in which the 3D model image 206d is moved from the spatial positions (indicated coordinates 206b and 206c) toward the operator in the depth direction. The amount of movement of the 3D model image 206d gradually decreases in the order from FIGS. 11A, 11B, and 11C. In this way, the adjusting unit 304c generates the 3D model image 206d that gradually decreases in the amount of back-and-forth movement in the depth direction with respect to the predetermined spatial positions (indicated coordinates 206b and 206c) in the 3D surgical image 206a, and the adjusting unit 304c finally stops the 3D model image 206d at the spatial positions (indicated coordinates 206b and 206c). This allows observers including an assistant to more naturally secure the recognition of the 3D model image 206d as a 3D image while closely observing the predetermined spatial positions (indicated coordinates 206b and 206c) in the 3D surgical image 206a. Thus, the implantation position of the 3D model image 206d can be recognized with higher accuracy.

The rotating unit 304d generates a 3D model image such that 3D model image 206d is rotated with respect to the predetermined spatial positions (indicated coordinates 206b and 206c) in the 3D surgical image 206a. The rotating unit 304d can perform processing for rotating the 3D model image 206d in addition to the processing functions of the depth processing unit 304b and the adjusting unit 304c. For example, a demonstration of display can be performed such that the 3D model image 206d is rotated, a hidden part of the 3D model image 206d is shown to recognize the overall shape of the model, and then the 3D model image 206d is largely moved in the depth direction to be finally adjusted and fit to a correct position.

Figure 12A:
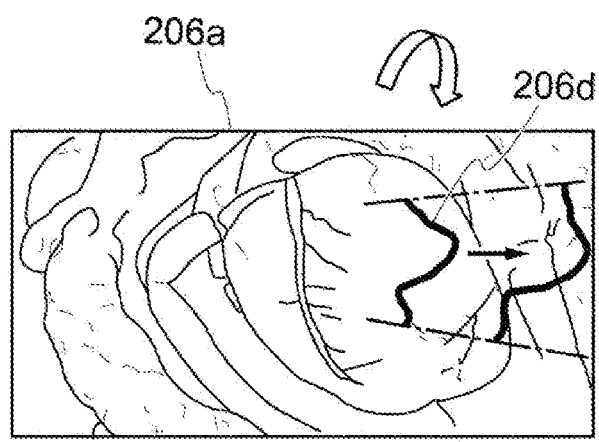
FIGS. 12A and 12B schematically illustrate a CG image generated by a rotating unit.
Figure 12B:
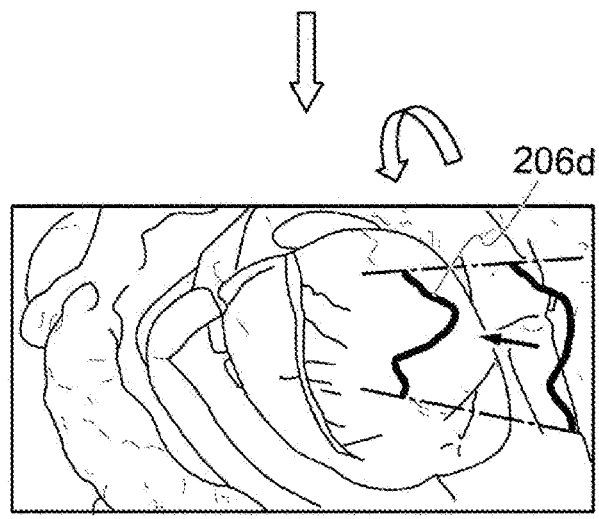

FIGS. 12A and 12B schematically illustrate a CG image generated by the rotating unit 304. FIG. 12A illustrates an example in which the 3D model image 206d rotated to the right while being moved from the spatial positions (indicated coordinates 206b and 206c) toward the operator in the depth direction. FIG. 12B illustrates an example in which the 3D model image 206d is rotated to the left while being moved from the spatial positions (indicated coordinates 206b and 206c) in a direction that separates from the operator in the depth direction. The 3D model image 206d is rotated thus, so that a hidden part of the 3D model image 206d can be shown to recognize the overall shape of the 3D model image 206d. This can more naturally secure the recognition of the 3D model image 206d as a 3D image while recognizing the overall shape of the 3D model image 206d.

The color processing unit 304e gradually changes the color of the 3D model image 206d with respect to the predetermined spatial positions (indicated coordinates 206b and 206c) in the 3D surgical image 206a. The color processing unit 304e can perform processing for changing the color of the 3D model image 206d in addition to the processing functions of the depth processing unit 304b, the adjusting unit 304c, and the rotating unit 304d. The color processing unit 304e can also apply colors to the 3D surgical image 206a.

Figure 13A:
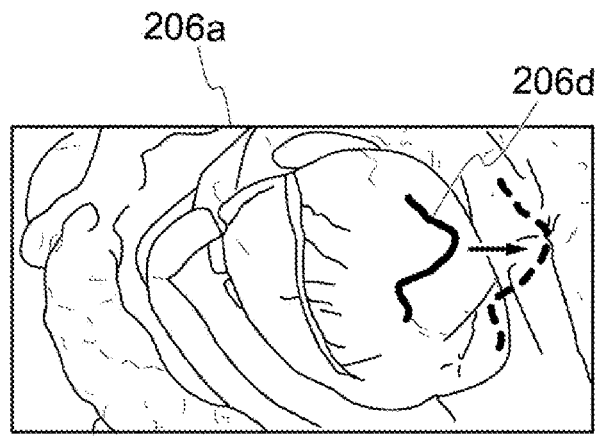
FIGS. 13A, 13B, and 13C schematically illustrate a CG image generated by a color processing unit.
Figure 13B:
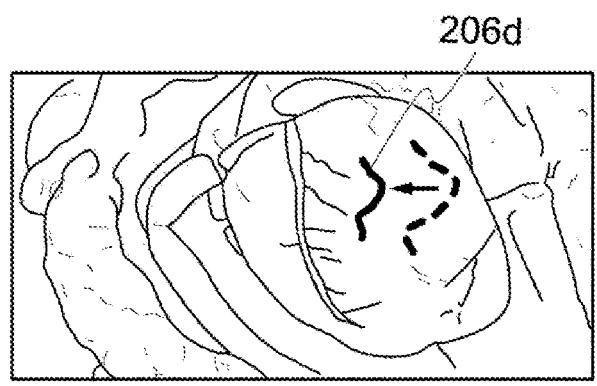
Figure 13C:

FIGS. 13A, 13B, and 13C schematically illustrate a CG image generated by the color processing unit 304e. FIG. 13A illustrates an example in which the 3D model image 206d is moved from the spatial positions (indicated coordinates 206b and 206c) toward the operator in the depth direction, and then the color of the 3D model image 206d is changed. In this example, a dotted line schematically indicates, for example, rainbow colors. The rainbow colors are, for example, six colors: red, orange, yellow, green, blue, and purple. The color processing unit 304e changes the color of the 3D model image 206d in the order of the six colors: red, orange, yellow, green, blue, and purple. FIG. 13B illustrates an example in which the 3D model image 206d is moved from the spatial positions (indicated coordinates 206b and 206c) in a direction that separates from the operator in the depth direction. In this example, a dotted line indicates, for example, colors different from those in FIG. 13A. FIG. 13C illustrates an example in which the 3D model image 206d is moved from the spatial positions (indicated coordinates 206b and 206c) toward the operator in the depth direction. In this example, a dotted line indicates, for example, colors different from those in FIGS. 13A and 13B. The display of rainbow colors provides the 3D model image 206d with liveliness, thereby enhancing the model.

Figure 14A:
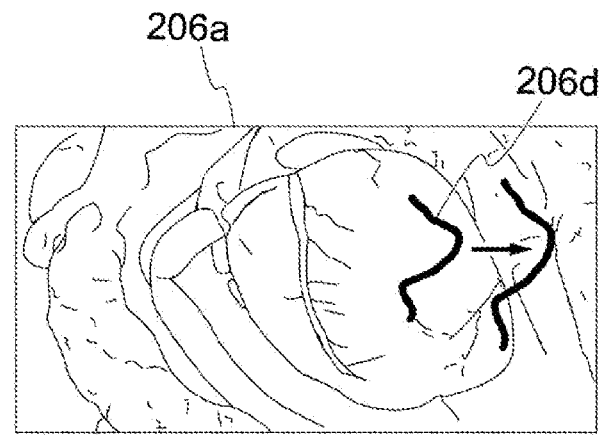
FIGS. 14A, 14B, and 14C schematically illustrate a 3D surgical image generated by translucent coloring on the 3D surgical image.
Figure 14B:
Figure 14B:
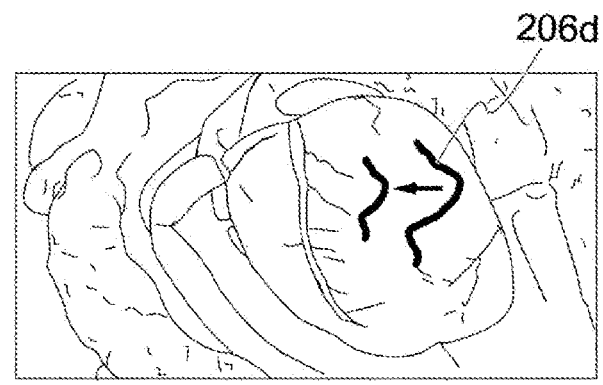
Figure 14C:
Figure 14C:
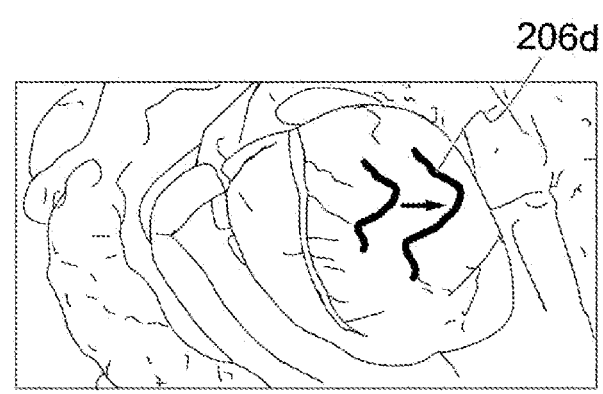

FIGS. 14A, 14B, and 14C schematically illustrate a 3D surgical image 2060a that is generated by translucent coloring on the 3D surgical image 206a by the color processing unit 304e. FIG. 14A illustrates an example in which the 3D model image 206d is moved from the spatial positions (indicated coordinates 206b and 206c) toward the operator in the depth direction. In this example, the 3D surgical image 2060a is generated by translucent coloring with, for example, pale blue on the 3D surgical image 206a. FIG. 14B illustrates an example in which the 3D model image 206d is moved from the spatial positions (indicated coordinates 206b and 206c) in a direction that separates from the operator in the depth direction. FIG. 14C illustrates an example in which the 3D model image 206d is moved from the spatial positions (indicated coordinates 206b and 206c) toward the operator in the depth direction. The translucent coloring on the 3D surgical image 206a reduces the sharpness of the 3D surgical image 206a and suppresses unnaturalness in texture between the 3D surgical image 2060a and the 3D model image 206d, thereby facilitating the recognition of the 3D model image 206d.

Figure 15:
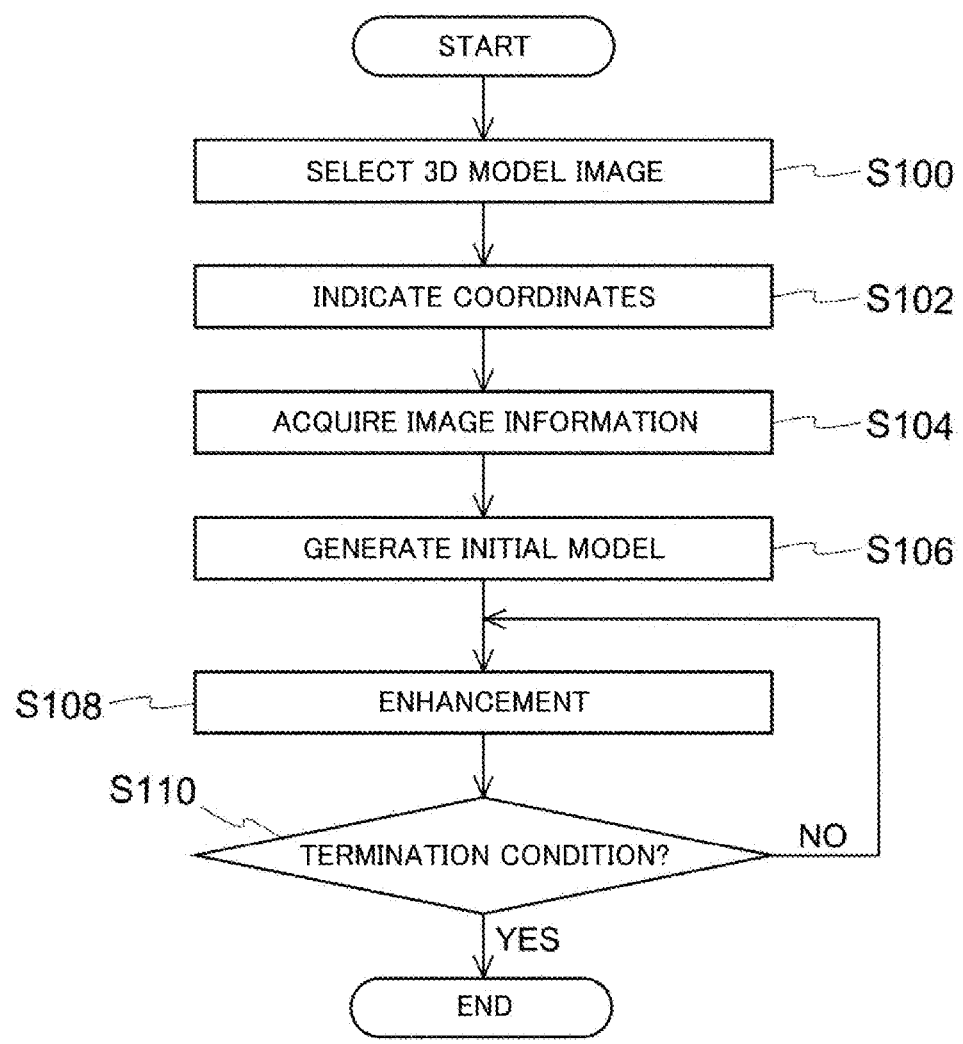

FIG. 15 is a flowchart of a processing example of the medical image processing system 1. As indicated in FIG. 15, the alignment unit 206 selects the 3D model image 206d in response to an operation via the operation input unit 500 (step S100). The alignment unit 206 then indicates the spatial positions (indicated coordinates 206b and 206c) in the 3D surgical image 206a in response to an operation via the operation input unit 500 (step S102). Subsequently, the indicated position calculating unit 208 sequentially calculates the indicated coordinates 206b and 206c in the 3D surgical image 206a generated in real time.

The acquisition unit 302 then acquires the 3D surgical image 206a, information on the selected 3D model image 206d, and the indicated coordinates 206b and 206c as image information (step S104). The acquisition unit 302 sequentially acquires the real-time 3D surgical image 206a and the indicated coordinates 206b and 206c.

Thereafter, the initial model generating unit 304a generates the initial model of the 3D model image 206d on the basis of image information set for the 3D model image 206d (step S106).

Subsequently, the superimposition unit 304 generates an enhanced image (e.g., one of FIGS. 10A, 10B, 11A, 11B, 11C, 12A, 12B, 13A, 13B, 13C, 14A, 14B, and 14C) for the 3D model image 206d and displays the enhanced image on the real-time 3D surgical image 206a (step S108). The superimposition unit 304 determines whether predetermined termination conditions are satisfied (step S110). If the termination conditions are not satisfied (No at step S110), the processing from step S108 is repeated. If the termination conditions are satisfied (Yes at step S110), the 3D model image 206d fixed at the indicated coordinates 206b and 206c is displayed, and then the processing is terminated.

As described above, the medical image processing system 1 according to the present embodiment is configured such that at the start of superimposition of the 3D model image 206d at the predetermined spatial positions (indicated coordinates 206b and 206c) when the 3D surgical image 206a is stereoscopically viewed, the superimposition unit 304 performs enhancement such that the location of the 3D model image 206d at the predetermined spatial positions (indicated coordinates 206b and 206c) is enhanced with respect to the 3D surgical image 206a or the 3D model image 206d. The enhancement facilitates the recognition of the 3D model image 206d as a 3D image. Once the 3D model image 206d is recognized as a 3D image, the image is recognized as a 3D image even after being fixed at the indicated coordinates 206b and 206c. Thus, the 3D surgical image 206a and the 3D model image 206d are integrally recognized as a 3D image with greater ease.

<<Application Example>>

The technique according to the present disclosure can be applied to various products. For example, the technique according to the present disclosure may be applied to a so-called microsurgery system that is used for performing microsurgery while observing an enlarged view of a small portion of a patient.

Figure 16:
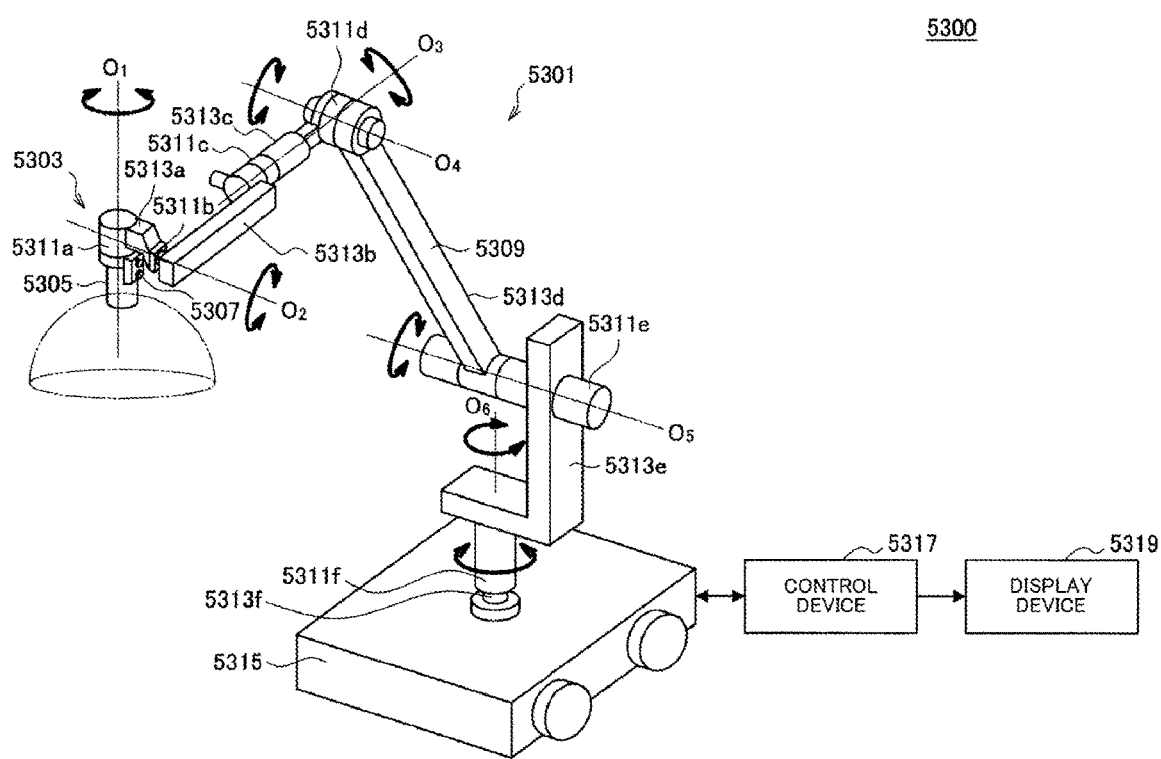

FIG. 16 illustrates an example of a schematic configuration of a microsurgery system 5300 to which the technique according to the present disclosure is applicable. Referring to FIG. 16, the microsurgery system 5300 includes a microscope apparatus 5301, a control device 5317, and a display device 5319. In the description of the microsurgery system 5300, "user" means any medical staff member, for example, a surgeon and an assistance who use the microsurgery system 5300.

The microscope apparatus 5301 includes a microscope unit 5303 for observing an enlarged view of an object to be observed (a surgical part of a patient), an arm part 5309 supporting the microscope unit 5303 at the distal end, and a base part 5315 supporting the proximal end of the arm part 5309.

The microscope unit 5303 includes a tubular part 5305 having a substantially cylindrical shape, an imaging unit (not illustrated) provided in the tubular part 5305, and an operation part 5307 provided on a part of the outer region of the tubular part 5305. The microscope unit 5303 is an electronic-imaging microscope unit (so-called video microscope unit) that electronically captures an image through an imaging unit.

At the aperture plane of the lower end of the tubular part 5305, a cover glass is provided to protect the imaging unit disposed in the tubular part 5305. Light from an object to be observed (hereinafter also referred to as observation light) passes through the cover glass and enters the imaging unit in the tubular part 305. The tubular part 5305 may contain, for example, a light source including an LED (Light Emitting Diode). During imaging, light may be emitted through the cover glass to the object to be observed.

The imaging unit includes an optical system that condenses observation light and an imaging element that receives the observation light condensed by the optical system. The optical system is configured with a combination of lenses including a zoom lens and a focus lens. The optical properties of the optical system are adjusted such that observation light forms an image on the light receiving surface of the imaging element. By receiving observation light and performing photoelectric conversion on the observation light, the imaging element generates a signal corresponding to the observation light, that is, an image signal corresponding to the observation light. The imaging element is, for example, an imaging element that has a Bayer array and can perform color imaging. As the imaging element, various known imaging elements such as a CMOS (Complementary Metal Oxide Semiconductor) image sensor or a CCD (Charge Coupled Device) image sensor may be used. The image signal generated by the imaging unit is transmitted as RAW data to the control device 5317. The image signal may be properly transmitted through optical communications. This is because a surgeon performs a surgical operation while observing the state of an affected part through the captured image at the site of the surgical operation and thus a moving image of a surgical part needs to be displayed as fast as possible to perform a safer and more reliable surgical operation. The transmission of the image signal through optical communications enables the display of a captured image with low latency.

The imaging unit may have a driving mechanism that moves the zoom lens and the focus lens of the optical system along the optical axis. The zoom lens and focus lens are properly moved by the driving mechanism, thereby adjusting the magnification of a captured image and a focal distance during imaging. The imaging unit may have various functions such as an AE (Auto Exposure) function and an AF (Auto Focus) function that are typically available for an electronic-imaging microscope unit.

Moreover, the imaging element may be configured as a so-called single-panel imaging unit having a single imaging element or a so-called multi-plate imaging unit having a plurality of imaging elements. In the case of a multi-plate imaging unit, for example, imaging elements may generate image signals for respective RGB and synthesize the image signals to obtain a color image. Alternatively, the imaging unit may be configured with a pair of imaging elements for acquiring right-eye and left-eye image signals for stereoscopic vision (3D display). The 3D display allows a surgeon to more accurately recognize the depth of a living tissue in a surgical part. If the imaging unit is configured as a multi-plate type, a plurality of optical systems can be provided for imaging elements.

The operation part 5307 includes, for example, a cross lever or a switch and serves as input means that receives an operation input of the user. Through the operation part 5307, the user can input, for example, an instruction to change a magnification of an observed image and a focal distance to an object to be observed. The driving mechanism of the imaging unit properly moves the zoom lens and the focus lens in response to the instruction, thereby adjusting the magnification and the focal distance. Moreover, through the operation part 5307, the user can input, for example, an instruction to switch the operation modes (an all-free mode and a fixing mode) of the arm part 5309. When moving the microscope unit 5303, the user is supposed to move the microscope unit 5303 while holding the tubular part 5305. Thus, in order to allow the user to operate the operation part 5307 while moving the tubular part 5305, the operation part 5307 is preferably located to be easily operated with a finger of the user holding the tubular part 5305.

The arm part 5309 is configured such that a plurality of links (first to sixth links 5313a to 5313f) are rotatably coupled to one another via a plurality of joints (first to sixth joints 5311a to 5311f).

The first joint 5311a has a substantially cylindrical shape that supports the upper end of the tubular part 5305 of the microscope unit 5303 at the distal end (lower end) of the first joint 5311a so as to rotate the upper end of the tubular part 5305 about a rotation axis (first axis $O_1$) parallel to the central axis of the tubular part 5305. In this case, the first joint 5311a can be configured such that the first axis $O_1$ agrees with the optical axis of the imaging unit of the microscope unit 5303. With this configuration, the rotation of the microscope unit 5303 about the first axis $O_1$ can change a field of view so as to rotate a captured image.

The first link 5313a securely supports the first joint 5311a at the distal end. Specifically, the first link 5313a is a rod member that is substantially L-shaped. The first link 5313a is connected to the first joint 5311a such that one side at the distal end of the first link 5313a extends perpendicularly to the first axis $O_1$; meanwhile, the end of the one side is in contact with the upper end of the outer surface of the first joint 5311a. The second joint 5311b is connected to the end of the other side at the proximal end of the substantially L-shaped first link 5313a.

The second joint 5311b has a substantially cylindrical shape that supports the proximal end of the first link 5313a at the distal end of the second joint 5311b so as to rotate the proximal end of the first link 5313a about a rotation axis (second axis $O_2$) perpendicular to the first axis $O_1$. The distal end of the second link 5313b is securely connected to the proximal end of the second joint 5311b.

The second link 5313b is a rod member that is substantially L-shaped. One side at the distal end of the second link 5313b extends perpendicularly to the second axis $O_2$; meanwhile, the end of the one side is securely connected to the proximal end of the second joint 5311b. The third joint 5311c is connected to the other side at the proximal end of the substantially L-shaped second link 5313b.

The third joint 5311c has a substantially cylindrical shape that supports the proximal end of the second link 5313b at the distal end of the third joint 5311c so as to rotate the proximal end of the second link 5313b about a rotation axis (third axis $O_3$) perpendicular to the first axis $O_1$ and the second axis $O_2$. The distal end of the third link 5313c is securely connected to the proximal end of the third joint 5311c. The rotation of the distal-end configuration including the microscope unit 5303 about the second axis $O_2$ and the third axis $O_3$ can move the microscope unit 5303 so as to change the position of the microscope unit 5303 in a horizontal plane. In other words, by controlling rotations about the second axis $O_2$ and the third axis $O_3$, the field of view of a captured image can be moved in a plane.

The third link 5313c is configured such that the distal end is substantially cylindrical. The proximal end of the third joint 5311c is securely connected to the cylindrical distal end such that the center axes of the third link 5313c and the third joint 5311c substantially agree with each other. The proximal end of the third link 5313c is shaped like a prism, and the fourth joint 5311d is connected to the end.

The fourth joint 5311d has a substantially cylindrical shape that supports the proximal end of the third link 5313c at the distal end of the fourth joint 5311d so as to rotate the proximal end of the third link 5313c about a rotation axis (fourth axis $O_4$) perpendicular to the third axis $O_3$. The distal end of the fourth link 5313d is securely connected to the proximal end of the fourth joint 5311d.

The fourth link 5313d is a rod member that is substantially linearly extended. The fourth link 5313d is securely connected to the fourth joint 5311d such that the fourth link 5313d extends perpendicularly to the fourth axis $O_4$; meanwhile, the end of the distal end of the fourth link 5313d is in contact with the side of the substantially cylindrical shape of the fourth joint 5311d. The fifth joint 5311e is connected to the proximal end of the fourth link 5313d.

The fifth joint 5311e has a substantially cylindrical shape that supports the proximal end of the fourth link 5313d at the distal end of the fifth joint 5311e so as to rotate the proximal end of the fourth link 5313d about a rotation axis (fifth axis $O_5$) parallel to the fourth axis $O_4$. The distal end of the fifth link 5313e is securely connected to the proximal end of the fifth joint 5311e. The fourth axis $O_4$ and the fifth axis $O_5$ are rotation axes that can vertically move the microscope unit 5303. The rotation of the distal-end configuration including the microscope unit 5303 about the fourth axis $O_4$ and the fifth axis $O_5$ can adjust the height of the microscope unit 5303, that is, a distance between the microscope unit 5303 and an object to be observed.

The fifth link 5313e is configured with a combination of a first member that is substantially L-shaped with one side extending in the vertical direction and the other side extending in the horizontal direction and a rod-like second member that vertically extends downward from a horizontally extending part of the first member. The proximal end of the fifth joint 5311e is securely connected near the upper end of a vertically extending part of the first member of the fifth link 5313e. The sixth joint 5311f is connected to the proximal end (lower end) of the second member of the fifth link 5313e.

The sixth joint 5311f has a substantially cylindrical shape that supports the proximal end of the fifth link 5313e at the distal end of the sixth joint 5311f so as to rotate the proximal end of the fifth link 5313e about a rotation axis (sixth axis $O_6$) parallel to the vertical direction. The distal end of the sixth link 5313f is securely connected to the proximal end of the sixth joint 5311f.

The sixth link 5313f is a rod member that extends in the vertical direction. The proximal end of the sixth link 5313f is securely connected to the top surface of the base part 5315.

The rotatable ranges of the first to sixth joints 5311a to 5311f are properly set so as to desirably move the microscope unit 5303. Thus, in the arm part 5309 configured thus, 3 degrees of freedom of translation and 3 degrees of freedom of rotation, that is, 6 degrees of freedom in total can be obtained for a movement of the microscope unit 5303. In this way, the arm part 5309 is configured to obtain 6 degrees of freedom for a movement of the microscope unit 5303, thereby freely controlling the position and posture of the microscope unit 5303 in the movable range of the arm part 5309. Thus, a surgical part can be observed from any angles, thereby facilitating a surgical operation.

The configuration of the illustrated arm part 5309 is merely exemplary. The number and shapes (lengths) of links constituting the arm part 5309, the number and placement positions of joints, and the directions of rotation axes may be properly designed to obtain a desired degree of freedom. For example, as described above, the arm part 5309 is preferably configured with 6 degrees of freedom in order to freely move the microscope unit 5303. The arm part 5309 may be configured with a higher degree of freedom (that is, a redundant degree of freedom). In the presence of a redundant degree of freedom in the arm part 5309, the posture of the arm part 5309 can be changed while the position and posture of the microscope unit 5303 are fixed. Thus, control with greater convenience can be provided for a surgeon. For example, the posture of the arm part 5309 can be controlled without interrupting the visibility of a surgeon who watches the display device 5319.

In this configuration, each of the first to sixth joints 5311a to 5311f can be provided with a driving mechanism, e.g., a motor and an actuator including an encoder for detecting a rotation angle at each of the joints. The driving of the actuator provided for each of the first to sixth joints 5311a to 5311f is properly controlled by the control device 5317, thereby controlling the posture of the arm part 5309, that is, the position and posture of the microscope unit 5303. Specifically, the control device 5317 can recognize the current posture of the arm part 5309 and the current position and posture of the microscope unit 5303 on the basis of information on the rotation angles of the joints, the rotation angles being detected by the encoder. By using the recognized information, the control device 5317 calculates a control value (e.g., a rotation angle or a generated torque) for each of the joints such that the microscope unit 5303 is moved in response to an operation input from the user, and the control device 5317 drives the driving mechanism of each of the joints according to the control value. At this point, the control method of the arm part 5309 by the control device 5317 is not limited and thus various known control methods such as force control or position control may be applied.

For example, a surgeon may properly input an operation via an input device, which is not illustrated, to properly control the driving of the arm part 5309 using the control device 5317 in response to the operation input, thereby controlling the position and the posture of the microscope unit 5303. According to this control, the microscope unit 5303 can be moved from any position to another position and then can be securely supported at the position after the movement. The input device is preferably an input device operable by a surgeon holding a surgical instrument with a hand. For example, a foot switch is preferably applied in consideration of convenience for the surgeon. An operation may be inputted in a noncontact manner on the basis of gesture detection or line-of-sight detection using a wearable device or a camera in an operating room. Thus, a user belonging to a clean area can operate a device belonging to an unclean area with a higher degree of freedom. Alternatively, the arm part 5309 may be operated by a so-called master slave method. In this case, the arm part 5309 can be remotely operated by a user through the input device installed at a location remote from an operating room.

If force control is applied, so-called power assist control may be performed to receive an external force from a user and drive the actuators of the first to sixth joints 5311*a* to 5311*f* so as to smoothly move the arm part 5309 in response to the external force. Thus, when the user holds the microscope unit 5303 to directly move the position of the microscope unit 5303, the user can move the microscope unit 5303 with a relatively small force. This can more intuitively move the microscope unit 5303 with a simpler operation, thereby improving user convenience.

The driving of the arm part 5309 may be controlled to perform a pivoting operation. The pivoting operation is an operation for moving the microscope unit 5303 such that the optical axis of the microscope unit 5303 is always directed toward a predetermined point (hereinafter referred to as a pivot point) on a space. The pivoting operation enables an observation of the same observation position in various directions, thereby observing an affected part in more detail. If the microscope unit 5303 is configured with a focal distance that is not adjustable, a pivoting operation is preferably performed while a distance is fixed between the microscope unit 5303 and the pivot point. In this case, the distance between the microscope unit 5303 and the pivot point may be adjusted to a fixed focal distance of the microscope unit 5303. Thus, the microscope unit 5303 moves on a hemispherical surface (schematically illustrated in FIG. 16) having a radius corresponding to a focal distance with respect to the pivot point, so that a clear image can be captured even when the observation direction is changed. If the microscope unit 5303 is configured with an adjustable focal distance, a pivoting operation may be performed with a variable distance between the microscope unit 5303 and the pivot point. In this case, for example, the control device 5317 may calculate a distance between the microscope unit 5303 and the pivot point on the basis of information on the rotation angles of the joints, the rotation angles being detected by the encoder, and then the focal distance of the microscope unit 5303 may be automatically adjusted on the basis of the calculation result. If the microscope unit 5303 is provided with the AF function, a focal distance may be automatically adjusted by the AF function each time a distance between the microscope unit 5303 and the pivot point is changed by a pivoting operation.

The first to sixth joints 5311*a* to 5311*f* may be provided with brakes for restricting the rotations. The operations of the brakes can be controlled by the control device 5317. For example, when the position and posture of the microscope unit 5303 are supposed to be fixed, the control device 5317 operates the brakes of the joints. This can fix the position and posture of the arm part 5309, that is, the position and posture of the microscope unit 5303 without driving the actuators, thereby reducing power consumption. When the position and posture of the microscope unit 5303 are supposed to be moved, the control device 5317 may release the brakes of the joints and drive the actuators according to a predetermined control method.

Such a braking operation can be performed in response to an operation input by the user via the operation part 5307. When the position and posture of the microscope unit 5303 are supposed to be moved, the user operates the operation part 5307 to release the brakes of the joints. This changes the operation mode of the arm part 5309 to the mode of freely rotating the joints (all-free mode). When the position and posture of the microscope unit 5303 are supposed to be fixed, the user operates the operation part 5307 to operate the brakes of the joints. This changes the operation mode of the arm part 5309 to the mode of restricting the rotations of the joints (fixing mode).

The control device 5317 controls the overall operations of the microsurgery system 5300 by controlling the operations of the microscope apparatus 5301 and the display device 5319. For example, the control device 5317 controls the driving of the arm part 5309 by operating the actuators of the first to sixth joints 5311*a* to 5311*f* according to a predetermined control method. Moreover, for example, the control device 5317 changes the operation mode of the arm part 5309 by controlling the braking operations of the first to sixth joints 5311*a* to 5311*f*. Furthermore, for example, the control device 5317 generates image data for display by performing various kinds of signal processing on the image signal acquired by the imaging unit of the microscope unit 5303 of the microscope apparatus 5301, and displays the image data on the display device 5319. In the signal processing, a variety of known signal processing such as development (demosaic processing), high image quality processing (e.g., band enhancement, super-resolution processing, NR (Noise Reduction) processing, and/or camera shake correction), and/or enlargement (i.e., electronic zooming) may be performed.

Communications between the control device 5317 and the microscope unit 5303 and communications between the control device 5317 and the first to sixth joints 5311*a* to 5311*f* may be either of wire or radio communications. In the case of wire communications, communications may be performed by an electric signal or optical communications may be performed. In this case, a transmission cable used for wire communications can be configured as an electric signal cable, an optical fiber, or a composite cable thereof according to the communication mode. In the case of radio communications, a transmission cable does not need to be routed in an operating room, and thus the transmission cable does not interfere with a movement of medical staff in an operating room.

The control device 5317 can be a processor, e.g., a CPU (Central Processing Unit) or a GPU (Graphics Processing Unit) or a microcomputer or a control board on which a processor and storage elements such as a memory are combined. The various functions are implemented by operating the processor of the control device 5317 according to a predetermined program. In the illustrated example, the control device 5317 and the microscope apparatus 5301 are separate devices. The control device 5317 may be installed in the base part 5315 of the microscope apparatus 5301 to be integrated with the microscope apparatus 5301. Alternatively, the control device 5317 may be configured with a plurality of devices. For example, the same functions as the control device 5317 may be implemented by providing each of the microscope unit 5303 and the first to sixth joints 5311*a* to 5311*f* of the arm part 5309 with a microcomputer or a control board and making connections to perform communication among the microscope unit 5303 and the first to sixth joints 5311*a* to 5311*f*.

The display device 5319 is provided in an operating room and displays an image, which corresponds to image data generated by the control device 5317, under the control of the control device 5317. In other words, an image of a surgical part captured by the microscope unit 5303 is displayed on the display device 5319. The display device 5319 may display various kinds of information on surgery, for example, body information on a patient and information on techniques instead of an image of a surgical part or in addition to an image of a surgical part. In this case, the display of the display device 5319 may be properly switched by a user operation. Alternatively, the display device 5319 may be a plurality of display devices, each of which displays an image of a surgical part and various kinds of information on surgery. Various known display devices, for example, a liquid crystal display device or an EL (Electro Luminescence) display device may be used as the display device 5319.

Figure 17:
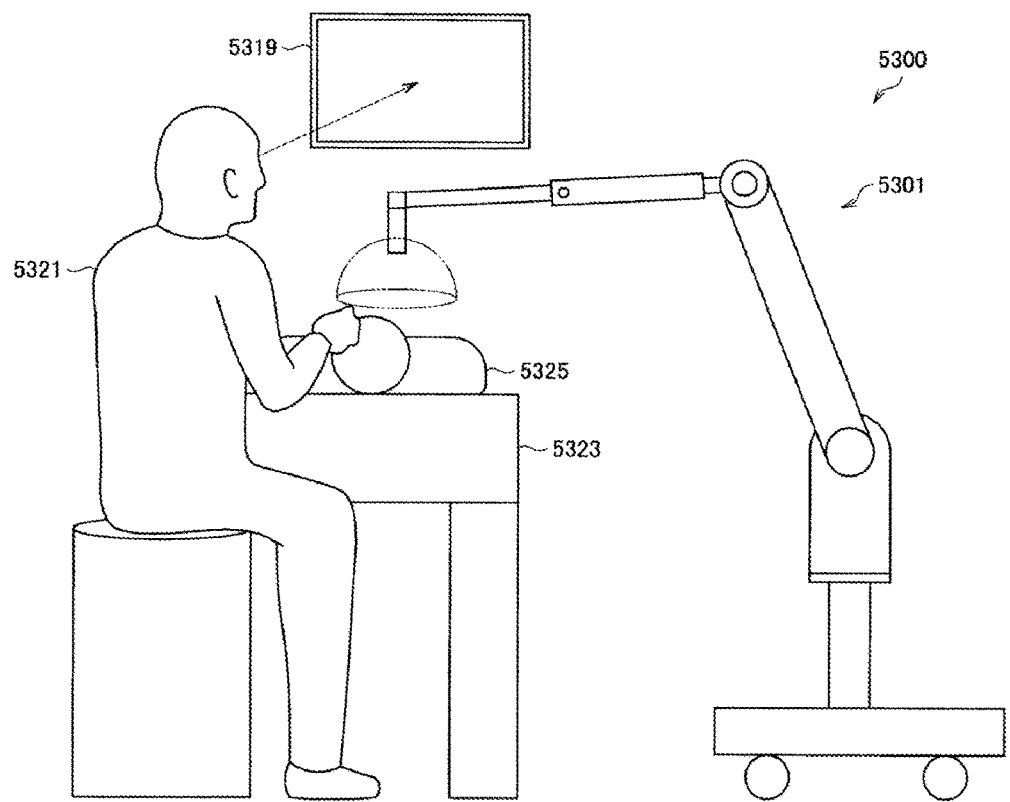

FIG. 17 illustrates a state of surgery using the microsurgery system 5300 illustrated in FIG. 16. FIG. 17 schematically illustrates a state in which a surgeon 5321 performs a surgical operation on a patient 5325 on a patient bed 5323 by using the microsurgery system 5300. In FIG. 17, for simplification, the control device 5317 is not illustrated and the microscope apparatus 5301 is simplified in the configuration of the microsurgery system 5300.

As illustrated in FIG. 17, by using the microsurgery system 5300 during a surgical operation, an image of a surgical part captured by the microscope apparatus 5301 is displayed as an enlarged image on the display device 5319 installed on a wall surface of an operating room. The display device 5319 is located to face the surgeon 5321. The surgeon 5321 performs various operations such as a resection of an affected part on the surgical part while observing a state of the surgical part through an image on the display device 5319.

The example of the microsurgery system 5300 to which the technique according to the present disclosure is applicable has been described above. Although the microsurgery system 5300 has been described as an example, a system to which the technique according to the present disclosure is applicable is not limited to this example. For example, the microscope apparatus 5301 can also act as a support arm device that supports another observation device or another surgical instrument instead of the microscope unit 5303 at the distal end. The observation device may be, for example, an endoscope. The surgical instrument may be forceps, tweezers, a pneumoperitoneum tube, or an energy treatment instrument for incising tissue and sealing a blood vessel by cauterization. The observation device and surgical instruments are supported by the support arm device, so that the positions can be fixed with higher stability and the workload of the medical staff can be lighter than in manual support by medical staff. The technique according to the present disclosure may be applied to such a support arm device that supports configurations other than a microscope unit.

The technique according to the present disclosure can be suitably applied to the control device 5317 in the forgoing configurations. Specifically, the application of the technique according to the present disclosure to the control device 5317 facilitates the recognition of the 3D model image 206*d* as a 3D image. Thus, an image of a surgical part can be obtained with ease of recognition, achieving a safer and more reliable surgical operation.

The present technique can be configured as follows:
(1) A medical image processing system includes: an acquisition unit that acquires a real-time 3D surgical image of an operation site stereoscopically viewable by a surgeon and a 3D model image that is a stereoscopic CG image associated with the 3D surgical image; and a superimposition unit that performs enhancement such that the location of the 3D model image at predetermined spatial positions is enhanced with respect to the 3D surgical image or the 3D model image at the start of superimposition of the 3D model image at the predetermined spatial positions when the 3D surgical image is stereoscopically viewed on the basis of information set for the 3D model image.
(2) The medical image processing system according to (1) further includes a display device configured to display the 3D surgical image and the 3D model image that are superimposed by the superimposition unit.
(3) The medical image processing system according to (1) or (2), wherein the superimposition unit generates the 3D model image that moves back and forth in the depth direction with respect to the predetermined spatial positions.
(4) The medical image processing system according to (3), wherein the superimposition unit generates the 3D model image that gradually decreases in the amount of back-and-forth movement in the depth direction with respect to the predetermined spatial positions.
(5) The medical image processing system according to (3) or (4), wherein the superimposition unit changes, according to the size of the 3D model image, an amount of back-and-forth movement in the depth direction with respect to the predetermined spatial positions.
(6) The medical image processing system according to (3) or (4), wherein the superimposition unit changes an amount of back-and-forth movement in the depth direction with respect to the predetermined spatial positions, according to the size of the 3D model image relative to the surgical 3D image.
(7) The medical image processing system according to any one of (3) to (5), wherein the superimposition unit rotates the 3D model image with respect to the predetermined spatial positions.
(8) The medical image processing system according to any one of (3) to (7), wherein the superimposition unit changes the color of the 3D model image with respect to the predetermined spatial positions.
(9) The medical image processing system according to (8), wherein the superimposition unit gradually changes the color of the 3D model image with respect to the predetermined spatial positions.
(10) The medical image processing system according to (1), wherein the superimposition unit changes at least one of the color and the spatial frequency of the 3D surgical image when performing the enhancement.
(11) The medical image processing system according to (1) further includes at least one of an endoscope and a surgical microscope that capture an original image used for generating the 3D surgical image.
(12) A surgical image control device includes: an acquisition unit that acquires a real-time 3D surgical image of an operation site stereoscopically viewable by a surgeon and a 3D model image that is a stereoscopic CG image associated with the 3D surgical image; and a superimposition unit that performs enhancement such that the location of the 3D model image at predetermined spatial positions is enhanced with respect to the 3D surgical image or the 3D model image at the start of superimposition of the 3D model image at the predetermined spatial positions when the 3D surgical image is stereoscopically viewed on the basis of information set for the 3D model image.
(13) A surgical image control method includes: acquiring a real-time 3D surgical image of an operation site stereoscopically viewable by a surgeon and a 3D model image that is a stereoscopic CG image associated with the 3D surgical image; and conducting superimposition that performs enhancement such that the location of the 3D model image at predetermined spatial positions is enhanced with respect to the 3D surgical image or the 3D model image at the start of superimposition of the 3D model image at the predetermined spatial positions when the 3D surgical image is stereoscopically viewed on the basis of information set for the 3D model image.

REFERENCE SIGNS LIST

1 Medical image processing system
206a 3D surgical image
206d 3D model image
302 Acquisition unit
304 Superimposition unit
400, 5041, 5319 Display device
5011 Endoscope
5301 Microscope apparatus

The invention claimed is:

1. A medical image processing system, comprising:
circuitry configured to:
acquire a real-time three-dimensional (3D) surgical image of an operation site stereoscopically viewable by a surgeon and a 3D model image that is a stereoscopic computer graphics (CG) image associated with the real-time 3D surgical image;
perform enhancement such that a location of the 3D model image at specific spatial positions is enhanced with respect to one of the real-time 3D surgical image or the 3D model image, at start of superimposition of the 3D model image at the specific spatial positions when the real-time 3D surgical image is stereoscopically viewed based on information set for the 3D model image; and
generate the 3D model image that moves back-and-forth in a depth direction with respect to the specific spatial positions in the real-time 3D surgical image.

2. The medical image processing system according to claim 1, further comprising a display device, wherein
the circuitry is further configured to superimpose the 3D model image on the real-time 3D surgical image, and
the display device is configured to display the real-time 3D surgical image and the 3D model image that are superimposed.

3. The medical image processing system according to claim 1, wherein the circuitry is further configured to generate the 3D model image that gradually decreases in an amount of the back-and-forth movement in the depth direction with respect to the specific spatial positions.

4. The medical image processing system according to claim 1, wherein the circuitry is further configured to change, based on a size of the 3D model image, an amount of the back-and-forth movement in the depth direction with respect to the specific spatial positions.

5. The medical image processing system according to claim 1, wherein the circuitry is further configured to change an amount of the back-and-forth movement in the depth direction with respect to the specific spatial positions, based on according to a size of the 3D model image relative to the real-time 3D surgical image.

6. The medical image processing system according to claim 1, wherein the circuitry is further configured to rotate the 3D model image with respect to the specific spatial positions.

7. The medical image processing system according to claim 1, wherein the circuitry is further configured to change a color of the 3D model image with respect to the specific spatial positions.

8. The medical image processing system according to claim 7, wherein the circuitry is further configured to gradually change the color of the 3D model image with respect to the specific spatial positions.

9. The medical image processing system according to claim 1, wherein the circuitry is further configured to change at least one of a color and a spatial frequency of the real-time 3D surgical image to perform the enhancement.

10. The medical image processing system according to claim 1, further comprising at least one of an endoscope and a surgical microscope configured to capture an original image used to generate the real-time 3D surgical image.

11. A surgical image control device, comprising:
circuitry configured to:
acquire a real-time three-dimensional (3D) surgical image of an operation site stereoscopically viewable by a surgeon and a 3D model image that is a stereoscopic computer graphics (CG) image associated with the real-time 3D surgical image;
perform enhancement such that a location of the 3D model image at specific spatial positions is enhanced with respect to one of the real-time 3D surgical image or the 3D model image, at start of superimposition of the 3D model image at the specific spatial positions when the real-time 3D surgical image is stereoscopically viewed based on information set for the 3D model image; and
generate the 3D model image that moves back-and-forth in a depth direction with respect to the specific spatial positions in the real-time 3D surgical image.

12. A surgical image control method, comprising:
acquiring a real-time three-dimensional (3D) surgical image of an operation site stereoscopically viewable by a surgeon and a 3D model image that is a stereoscopic computer graphics (CG) image associated with the real-time 3D surgical image;
performing enhancement such that a location of the 3D model image at specific spatial positions is enhanced with respect to one of the real-time 3D surgical image or the 3D model image, at start of superimposition of the 3D model image at the specific spatial positions when the real-time 3D surgical image is stereoscopically viewed based on information set for the 3D model image; and
generating the 3D model image that moves back-and-forth in a depth direction with respect to the specific spatial positions in the real-time 3D surgical image.

* * * * *